(12) United States Patent
Garcia Mansilla et al.

(10) Patent No.: US 10,791,788 B2
(45) Date of Patent: *Oct. 6, 2020

(54) HEADPHONE AND HELMET ASSEMBLY

(71) Applicant: UNIT 1 GEAR, INC., Wilmington, DE (US)

(72) Inventors: Juan Garcia Mansilla, Buenos Aires (AR); Javier Mariano Bertani, Buenos Aires (AR)

(73) Assignee: UNIT 1 GEAR, INC., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/531,957

(22) Filed: Aug. 5, 2019

(65) Prior Publication Data

US 2019/0350301 A1    Nov. 21, 2019

Related U.S. Application Data

(63) Continuation of application No. 16/072,001, filed as application No. PCT/US2018/019065 on Feb. 21, 2018, now Pat. No. 10,398,188.

(60) Provisional application No. 62/461,774, filed on Feb. 21, 2017.

(51) Int. Cl.
| | |
|---|---|
| *H04R 25/00* | (2006.01) |
| *A42B 3/30* | (2006.01) |
| *A42B 3/16* | (2006.01) |
| *A61F 11/14* | (2006.01) |
| *H04R 1/10* | (2006.01) |
| *H04R 5/033* | (2006.01) |

(52) U.S. Cl.
CPC .................. *A42B 3/30* (2013.01); *A42B 3/16* (2013.01); *A61F 11/14* (2013.01); *H04R 1/1008* (2013.01); *H04R 1/1041* (2013.01); *H04R 1/1066* (2013.01); *H04R 5/0335* (2013.01); *H04R 1/1075* (2013.01); *H04R 2201/023* (2013.01)

(58) Field of Classification Search
CPC .. A42B 3/30; A42B 3/16; A61F 11/14; H04R 1/1008; H04R 1/1041
See application file for complete search history.

(56) References Cited

U.S. PATENT DOCUMENTS

| | | | |
|---|---|---|---|
| 3,864,756 A | 2/1975 | Desimone | |
| 3,910,269 A * | 10/1975 | Ansite | A42B 3/228 128/201.24 |
| 3,943,572 A * | 3/1976 | Aileo | A42B 3/166 2/415 |

(Continued)

OTHER PUBLICATIONS

WIPO, ISR/WO for PCT/US2018/019065, dated May 3, 2018.

(Continued)

*Primary Examiner* — Simon King
(74) *Attorney, Agent, or Firm* — Hodgson Russ LLP

(57) ABSTRACT

The present disclosure can be embodied by a detachable assembly, for example a helmet and headphone assembly. A locking assembly can be configured to removably attach the headphones to the helmet in a locked position. In the locked position, the headphones can be locked horizontally onto the helmet, and a portion of ear cups of the headphones may be received at least partially through a pair of ear cup receiving apertures that extend through a shell of the helmet.

19 Claims, 41 Drawing Sheets

(56) References Cited

U.S. PATENT DOCUMENTS

| | | | |
|---|---|---|---|
| 4,453,277 A * | 6/1984 | Durand | A42B 3/14 2/416 |
| 4,516,274 A * | 5/1985 | Buckland | A42B 3/166 2/209 |
| 6,148,446 A | 11/2000 | Leight | |
| 6,546,264 B1 * | 4/2003 | Kennedy | A42B 3/30 379/430 |
| 7,853,035 B2 | 12/2010 | Tsunoda et al. | |
| 8,176,574 B2 | 5/2012 | Bryant et al. | |
| 9,036,855 B2 | 5/2015 | Shah | |
| 2006/0147052 A1 * | 7/2006 | Wikel | H04R 5/0335 381/74 |
| 2007/0261153 A1 * | 11/2007 | Wise | A42B 3/044 2/423 |
| 2009/0260135 A1 | 10/2009 | Haselmayer | |
| 2010/0083413 A1 | 4/2010 | McGovern | |
| 2011/0314594 A1 * | 12/2011 | Rogers | A42B 3/04 2/421 |
| 2013/0061376 A1 * | 3/2013 | Halfaker | A42B 3/166 2/414 |
| 2013/0064412 A1 * | 3/2013 | Alstad | H04R 1/1033 381/380 |
| 2013/0219598 A1 | 8/2013 | Pfanner et al. | |
| 2016/0007112 A1 * | 1/2016 | Broadley | H04R 1/1066 381/72 |
| 2016/0095376 A1 * | 4/2016 | Schrader | A42B 3/166 2/410 |
| 2017/0150769 A1 * | 6/2017 | Lebel | A42B 3/30 |
| 2017/0332720 A1 * | 11/2017 | Zimmer | A42B 3/10 |
| 2018/0199652 A1 * | 7/2018 | Vaccaro | A42B 3/003 |
| 2019/0357620 A1 * | 11/2019 | Rogers | G02B 23/12 |

OTHER PUBLICATIONS

Contact, Soundshield-Helmet and Headphones Combined-Sneak Peek!, Feb. 14, 2017, retrieved on Jul. 23, 2018. Retrieved from Internet: <URL: https://www.youtube.com/watch?v=ysmF1aif5Pc>.

* cited by examiner

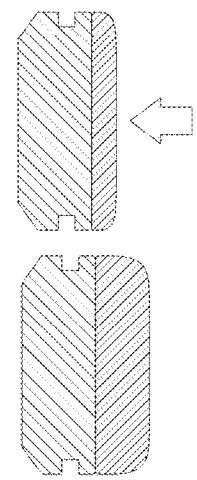
Fig. 13E
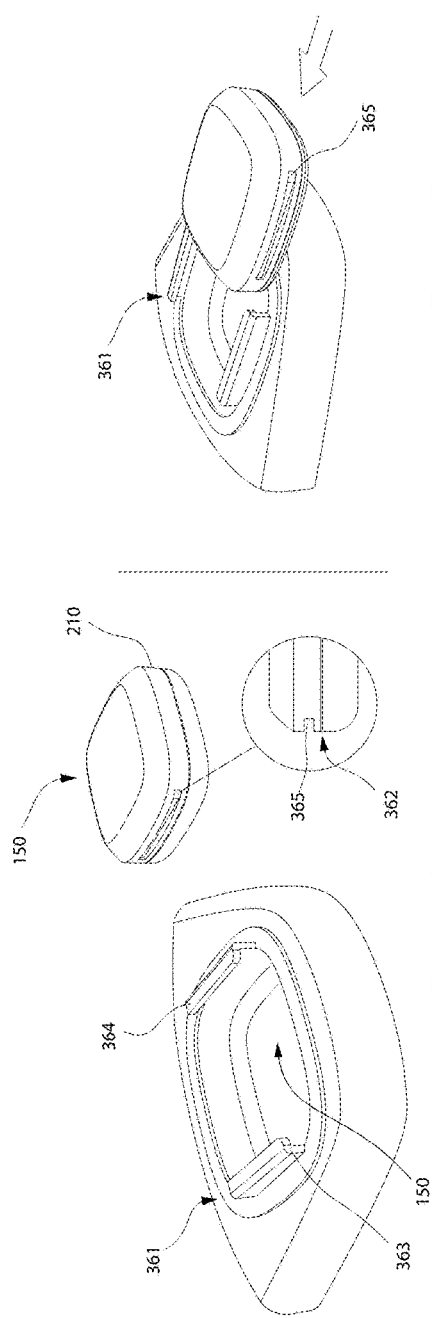
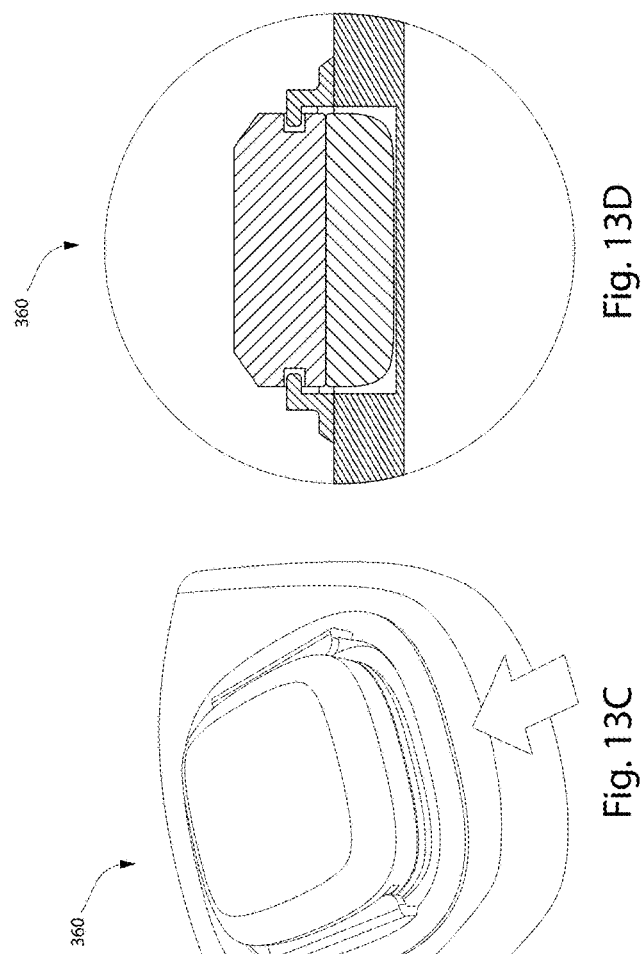

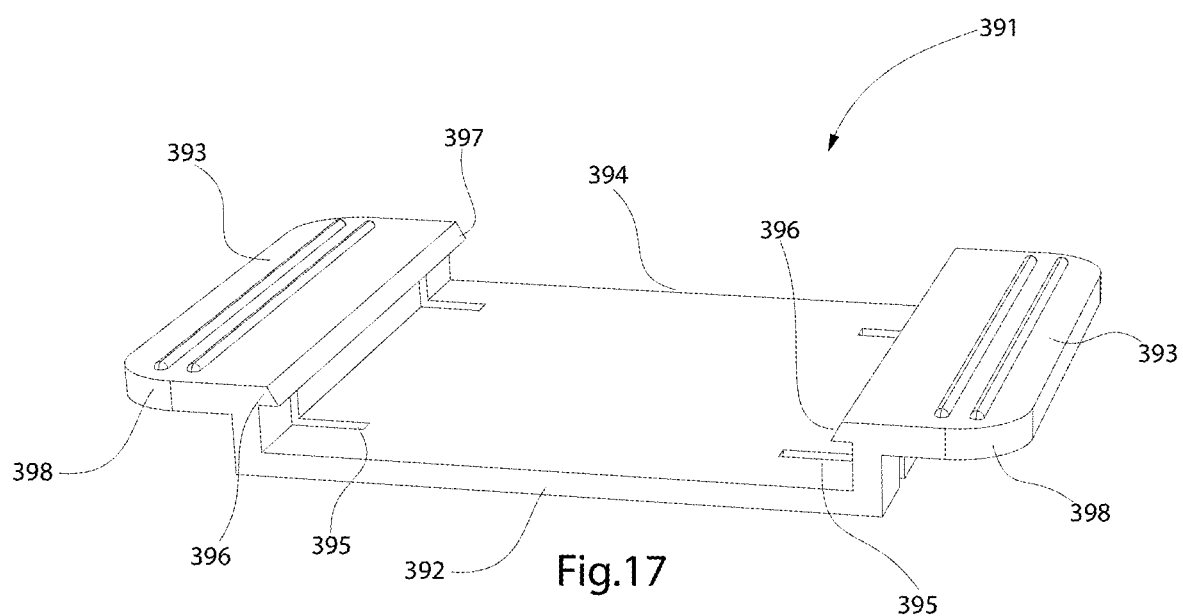

HEADPHONE AND HELMET ASSEMBLY

CROSS-REFERENCE TO RELATED APPLICATIONS

This application is a continuation of U.S. application Ser. No. 16/072,001, filed Jul. 23, 2018, which is a U.S. national phase application of International Patent Application No. PCT/CN2018/019065, filed Feb. 21, 2018, which claims priority to U.S. Provisional Application No. 62/461,774, filed on Feb. 21, 2017. The entire disclosures of the aforementioned applications are incorporated herein by reference.

FIELD OF THE DISCLOSURE

The present disclosure relates to headphone and helmet assemblies.

BACKGROUND OF THE DISCLOSURE

Conventional portable audio systems often include a pair of headphones that are connected to a media player for example by one or more wires or by wireless technology. It is increasingly common for users to use portable audio systems when engaging in outdoor activities. While the media player in any given portable audio system can be used in a variety of settings, it is often the case at the headphones employed are not as versatile. For example, in-ear headphones (also commonly referred to as also "earbuds") may provide for portability, but such headphones may provide poor audio quality, be uncomfortable, or both. While larger, over-the-ear headphones may be more comfortable, they may be offered to wear with outdoor gear such as goggles. For example, it is increasingly common for outdoor enthusiasts, such as skiers and snowboarders, to use portable audio systems when engaging in outdoor activities, such as skiing and snowboarding. In most cases, skiers and snowboarders favor smaller, in-ear style headphones because helmets, ski goggles, car protectors, hoods, and headbands can more easily be worn over such headphones Although the user gains portability during other activities with in-ear style headphones, the user may sacrifice on quality and comfort as in-ear headphones may provide poor audio quality and/or be uncomfortable. Moreover, in-ear style headphones may fall out of the user's ear during participation in the outdoor activity, thus frustrating the user and preventing the user from enjoying the portable audio system during the activity.

Due to the disadvantages with in-ear style headphones, the user may choose to use larger, over-the-ear style headphones when not participating in outdoor activities. For example, a user may use the over-the-ear headphones in a home, school, or office environment. The over-the-ear style headphones may provide better sound quality and comfort for indoor use, but typically the over-the-ear style headphones are not compatible with outdoor activities because helmets, ski goggles, ear protectors, and headbands may interfere with use of over the ear headphones.

Therefore, although the user uses the same media player in both instances, the user will likely need at least two different sets of headphones for the two different use environments. In particular, it is not uncommon for users of portable audio systems have several different sets of headphones each of which are used in different environments.

SUMMARY OF THE DISCLOSURE

The present disclosure can be embodied by a detachable assembly, for example a helmet and headphone assembly. The headphones can include a headband, ear cups, and a housing. The housing can define legs that extend between each of the ear cups and the headband. The helmet can provide protection for a user, and include a chinstrap, a shell, and a pair of ear cup receiving apertures extending fully through the shell. A locking assembly can be configured to removably attach the headphones to the helmet in a locked position. The pair of ear cup receiving apertures is configured to receive a respective one of the ear cups at least partially therethrough in the locked position. In the locked position, the headphones can be locked horizontally such that a longitudinal axis of the headphones lies at a locking angle that is ±20° from a second axis, the second axis extending from the user's eye and ear when the helmet is on the user, the longitudinal axis extending between each ear cup to a central apex of the headband.

According to certain embodiments of the present disclosure, at least a portion of the legs of the headphones can be disposed within the shell of the helmet in the locked position.

The present disclosure describes various locking assemblies. According to an embodiment, the locking assembly may include one or more male members and one or more female members configured to mate with the one or more male members. The one or more male members may be located adjacent the pair of ear cup receiving apertures. The one or more female members can be located on the ear cups. The locking assembly can include one or more flexible mating features that interlock with one another in a frictional manner.

According to other embodiments, the locking assembly can be a biased locking assembly having one or more slidable male members that are biased toward one or more female members in the locked position.

Another embodiment of the present disclosure provides for a rotational locking assembly having one or more rotational latch members and one or more fixed catch members. The one or more rotational latch members can be disposed within the helmet and the one or more fixed catch members are located on the ear cups. The one or more rotational latch members can includes two disks, each of the two disks having a central aperture defined by an inner edge. Each of the two disks can be rotationally mounted about each of the pair of ear cup receiving apertures between an unlocked position and the locked position. The central aperture can be concentric with each of the pair of ear cup receiving apertures. Furthermore, in the unlocked position, the inner edge can be located fully about each one of the pair of ear cup receiving apertures, and in the locked position, the inner edge can be positioned at least partially within each one of the pair of ear cup receiving apertures.

The one or more rotational latch members may include an arm disposed outside of the helmet and configured to allow the user to rotate the one or more rotational latch members between the locked position and the unlocked position. In the locked position, the arm can be located closer to the headband than in the unlocked position.

In another embodiment, the headphones can be rotated about the pair of ear cup receiving apertures to move the headphones between an unlocked position and the locked position.

According to another embodiment, a sliding locking assembly is provided having one or more male latch members defined by a pair of parallel, linear protrusions fixed adjacent to each one of the pair of ear cup receiving apertures, and one or more female catch members that receive the one or more male latch members in the locked position.

The detachable assembly described herein can further include a headphone leg locking assembly having male latch members located on the helmet, and female catch members located on the legs. The male latch members can be configured to removably attach the legs to an inner surface of the helmet in the locked position.

In certain embodiments, the detachable assembly can also include an alignment feature configured to align the headphones relative to the helmet in the locked position. The alignment feature may have a side edge of the headband that is configured to mate with a rear exterior edge of the helmet.

According to another embodiment, at least one of the ear cups includes an input control device configured to control a media source. At least one of the ear cups includes an inner piece and an outer piece, the inner piece housing a speaker for playing sound from the media source. The outer piece can include a rotational element configured to rotate relative to the inner piece. The input control device can include the rotational element, and rotating the rotational element relative to the inner piece can adjust a volume of media being played by the media source. The rotational element can have a plurality of teeth, and a first sensor element and a second sensor element may be disposed on opposite sides of the plurality of teeth. The first sensor element can include an infrared emitter and the second sensor element can include two or more light detectors.

In another embodiment, a bottom portion of the legs adjacent each of the ear cups are angled such that the ear cups can be fixed in a non-parallel position that corresponds to an angled outer surface of the shell of the helmet. For example, each of the ear cups can be angled relative to the headband at an angle between 2-5°. The ear cups can include an inner portion and an outer portion, where the inner portion is pivotably mounted to the inner portion. The inner portion may be capable of pivoting to a pivoting position that is up to 2-6° from an unpivoted position.

BRIEF DESCRIPTION OF THE DRAWINGS

The nature and mode of operation of the present disclosure will now be more fully described in the following detailed description of the disclosure taken with the accompanying drawing figures, in which:

FIGS. 13A-13C are perspective views illustrating a process of attaching headphones to a helmet with a sliding locking assembly in accordance with an embodiment of the present disclosure;

FIG. 13D is a cross-sectional view of FIG. 13C showing the headphones and helmet in a locked position;

FIG. 13E is a cross-sectional view of the ear cups of FIG. 12B illustrating the compression of the inner piece of the ear cup;

FIG. 17 is a perspective a leg locking assembly in accordance with another embodiment of the present disclosure;

DETAILED DESCRIPTION OF THE DISCLOSURE

Figure 1:
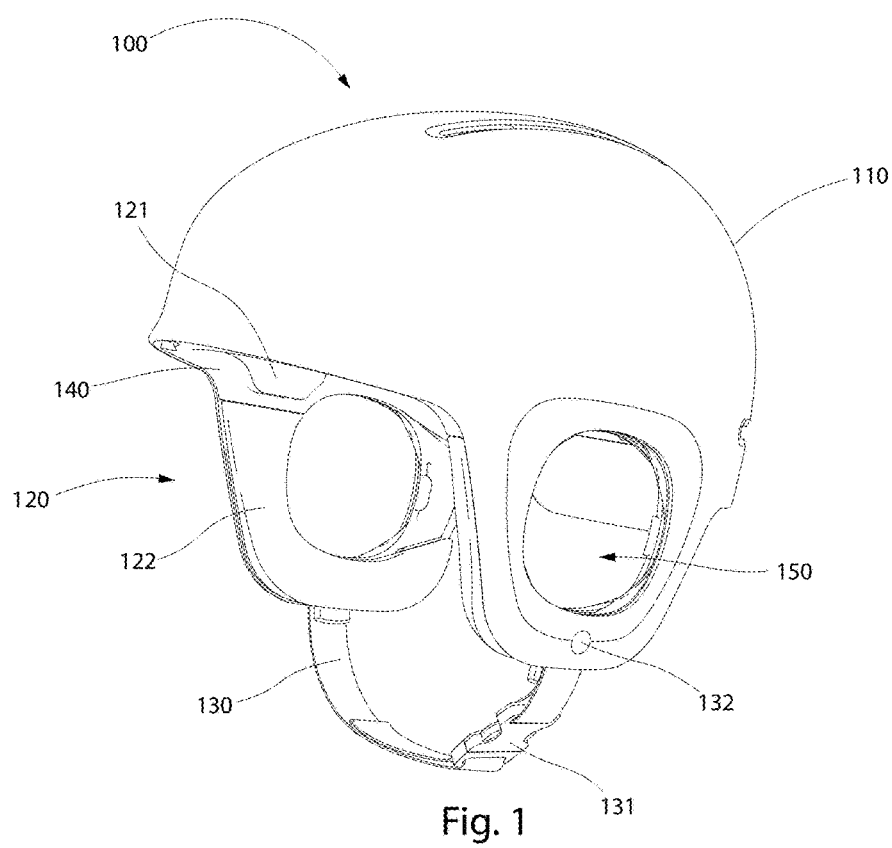
FIG. 1 is a perspective view of a helmet in accordance with an embodiment of the present disclosure.
Figure 2:
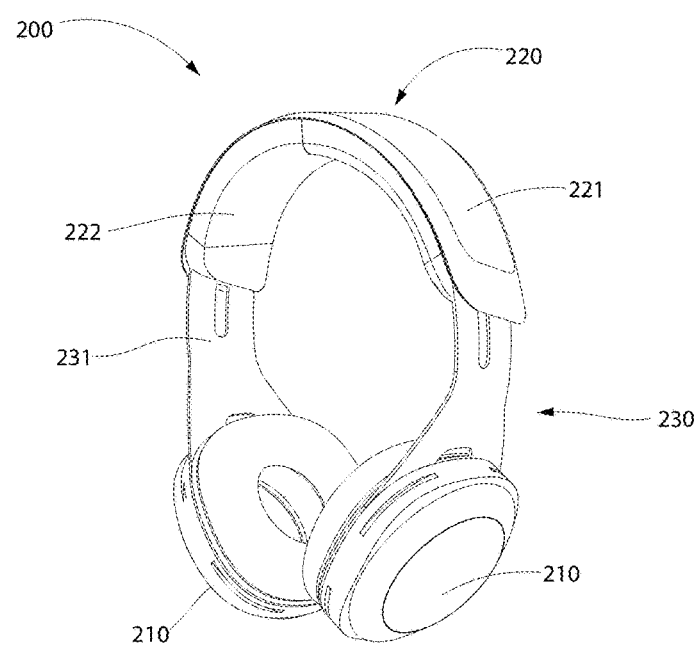
FIG. 2 is a perspective view of headphones in accordance with an embodiment of the present disclosure.

FIG. 1 shows a helmet 100 and FIG. 2 shows headphones 200 designed to be removably attachable to the helmet 100. A helmet 100 according to an embodiment of the present disclosure can include an outer shell 110, inner padding 120, and a chin strap 130. The inner padding 120 can include upper pads 121, and cheek pads 122. The chin strap 130 can include a buckle 131 and be attached via a fastener 132.

In one embodiment, the outer shell 110 of the helmet can be made of a hard plastic that provides high-impact resistance (especially at low temperatures), highway resistance, and high scratch resistance. For example, the outer shell 110 can be made from or include acrylonitrile butadiene styrene. The inner shell 140 can be made of a closed-cell foam material, such as expanded polystryrene. The thickness of the outer shell 110 and the inner shell 140 can vary depending upon the desired application. As one example, the outer shell 110 can have a thickness that is smaller than the thickness of the inner shell 140. In one particular example, the outer shell can be 3 mm thick and the inner shell 140 can be between 15-25 mm thick.

The helmet 100 can include ear cup receiving apertures 150, which receive ear cups 210 of the headphones therethrough. The helmet 100 can also include including locking assemblies, which allow the headphones to be removably attachable to the helmet 100 as described in further detail throughout the present disclosure.

The padding 120 of the helmet 100 can be made of a soft foam material. In one particular example, the upper pads 121 can be made of a 10 mm thick foam material and the cheek pads 122 can be made of a 35 mm thick foam material. The chin strap 130 of the helmet 100 can be made of a fabric, for example a nylon fabric, and the approximately 20 mm wide. The buckle 131 of the chin strap 130 can be made of plastic, for example, polyoxymethylene plastic.

With reference to FIG. 2, headphones according to an embodiment of the present disclosure can be over-the-ear style headphones, including a headband, a base housing 230, and ear cups 210.

The headband 220 can include an outer headband 221 and an inner headband 222. The outer headband 221 can be made of a durable plastic material that provides rigidity, such as a polycarbonate and/or polybutylene terephthalate plastic material. The outer headband 221 can therefore be used to support the inner headband 22, which receives a user's head during use. The inner headband 222 can be cushioned for comfortable use by a user. In one particular example, the inner headband is made of silicone.

The base housing 230 of the headphones can serve to house the various components of the headphones, including the headband 220 and ear cups 210. In one example, the base housing 230 can define legs 231 (e.g. either one continuous leg 231 having two sides or two independent legs 231) which connect the headband to the ear cups 210. The base housing 230 can be made out of any suitable material, including plastic and/or metals. In one particular example, the base housing 230 can be made of stainless steel that is approximately 1.2 mm thick. The legs 231 can include adjustment mechanisms for adjusting the length of the headband 220 relative to the ear cups 210 to accommodate different sized heads of users. For example, there may be two legs 231 that slide independently within the headband 220 and/or each of the ear cups 210 may slide along the legs 231.

The ear cups 210 of the headphone contain speakers configured to play sounds to the user. The headphones may be connected to a media source, such as a digital music player or a mobile phone, with a physical wire or wirelessly (e.g. Bluetooth, Wi-Fi, or another wireless protocol). In some embodiments, the headphones may also contain a microphone configured to capture voice commands or audio signals from the user. In some embodiments, the headphones may include controls that permit the user to control the media source. This can include controls to allow the user to change the volume, skip ahead in a music track, mute, disable the media source, receive phone calls, or input a voice command.

As previously noted, the headphones of the present disclosure can be removably attachable to the helmet via locking assembly. The locking assembly can include a series of mating features that interlock in a removably attachable fashion. In one example, the locking assembly can rely on flexible mating features that interlock with one another in a frictional manner (e.g. "snap-fit"). There are a number of variations of frictional locking arrangements, including cantilever, torsional and annular, and the present disclosure should not be read to be limited to one or more of these frictional locking arrangements. In some embodiments, the locking assembly may be made of a suitable material that has desirable coefficient of friction, high resistance, and high scratch resistance. In one particular example, a nylon polyamide may be used (e.g. 6/66).

Figure 3A:
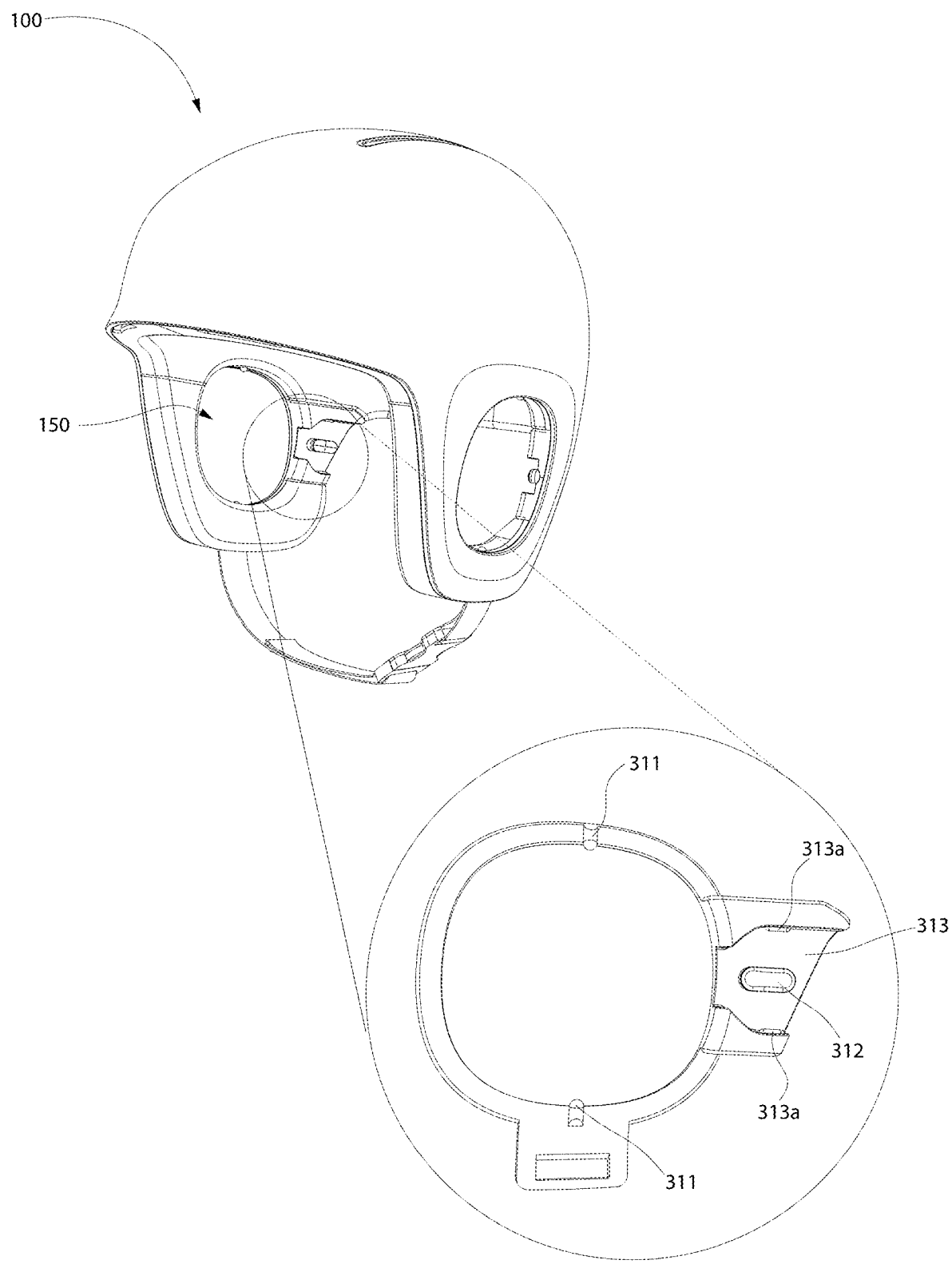
FIG. 3A is a combination perspective and detail view of a helmet with a snap-fit locking assembly in accordance with an embodiment of the present disclosure.
Figure 3B:
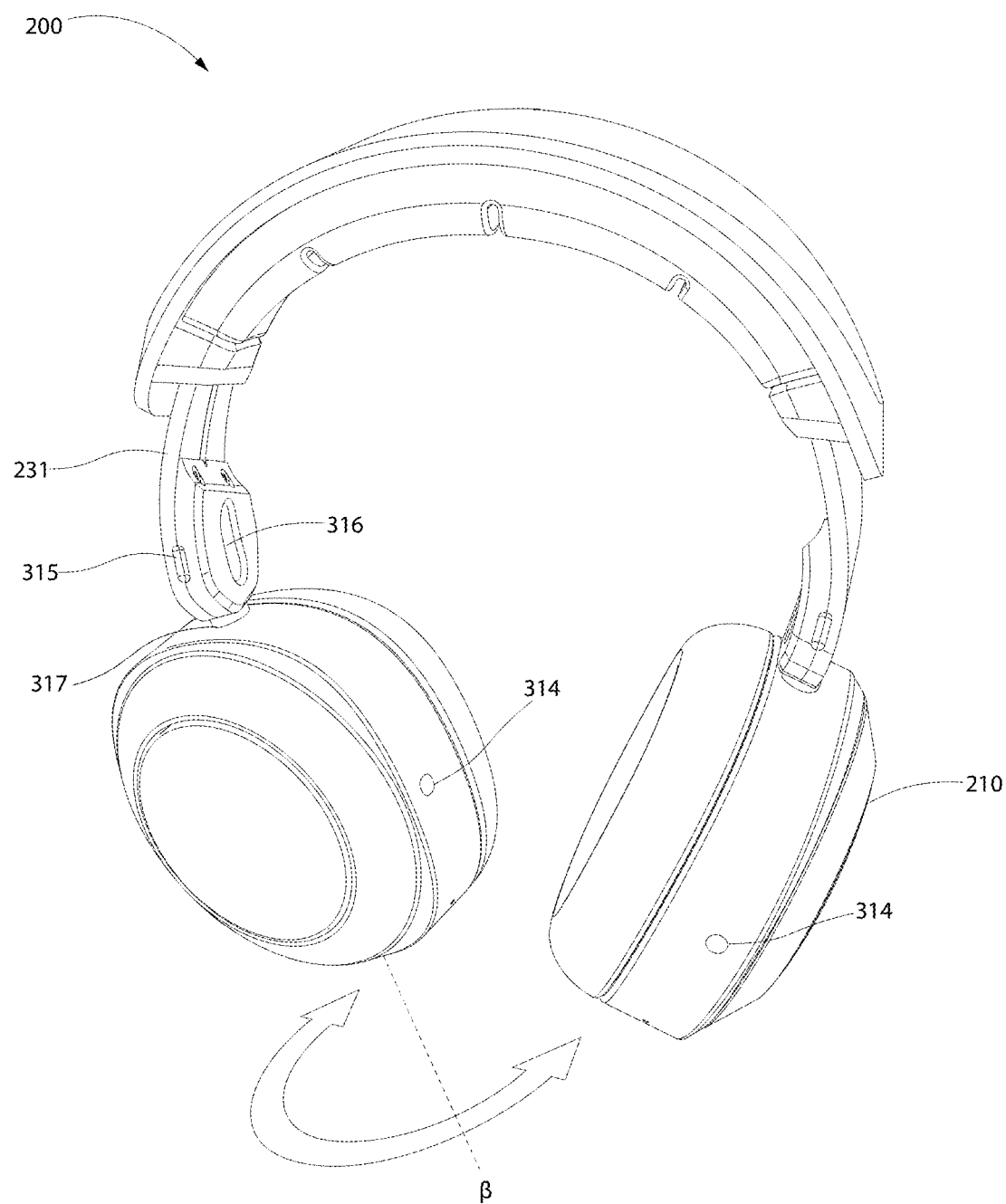
FIG. 3B is a perspective view of headphones for use with the helmet of FIG. 3A.

FIGS. 3A and 3B depict one particular embodiment of a snap-fit locking assembly where respective protrusions and/or recesses can be provided on the helmet 100 and headphones. Specifically, helmet 100 is provided with two protrusions 311 located about the ear cup receiving apertures 150. The protrusions 311 mate with respective recesses 314 provided on the headphones 200, for example, located on an outer perimeter of each cup 210. The present disclosure is not limited to the specific arrangement of recesses and protrusions shown in FIGS. 3A-3B, for example, protrusions could alternatively be located on the headphones, and recesses can be provided on the helmet, or both the headphones and helmet can include both recesses and protrusions.

In order to assist with alignment of the headphones relative to the helmet 100, the helmet 100 can include alignment features. For example, the helmet 100 includes two ear cup receiving apertures 150 that are sized and arranged to receive respective ear cups 210 of the headphones 200. The helmet 100 can also include additional alignment features to receive other portions of the headphones in order to align and maintain the headphones in a locked position that are separate and apart from the locking assemblies described herein. For example, the helmet 100 can include a trough 313 that receives the legs 231 of the helmet 100.

The trough 313 can include one or more protrusions 313a, which mate with one or more respective recesses 315 formed in each leg 231 of the headphones 200. The trough 313 can further include an alignment feature 312 for properly positioning the headphones within the trough 313. The alignment feature 312 (e.g. a track-shaped protrusion) can mate with a corresponding alignment feature 316 (e.g. a trough) on leg 231. The respective alignment features may also serve to assist in locking the headphones to the helmet in a locked position.

In order to lock the headphones 200 with helmet 100 in the embodiments shown in FIGS. 3A-3B, it may be necessary to have ear cups 210 that rotate relative to legs 231 in order to accommodate a difference in rotational position of the ear cups 210 when worn by a user (i.e. without a helmet) and when locked into the locked position on a helmet. FIG. 3B shows an example of ear cups 210, which are pivotably connected to the legs 231 via pivot 317 allow for rotation about axis β.

Another example of a locking assembly according to the present disclosure is a biased locking assembly. A biased locking assembly can include one or more mating features that are biased (e.g. via a spring) relative to one another for maintaining the headphones in a locked position relative to the helmet. A release member may be provided to release the biased lock. Corresponding mating features, such as protrusions and recesses can further assist in aligning the headphones and helmet relative to one another so that the headphones can be placed in a locked position with the biased locking assembly.

Figure 4A:
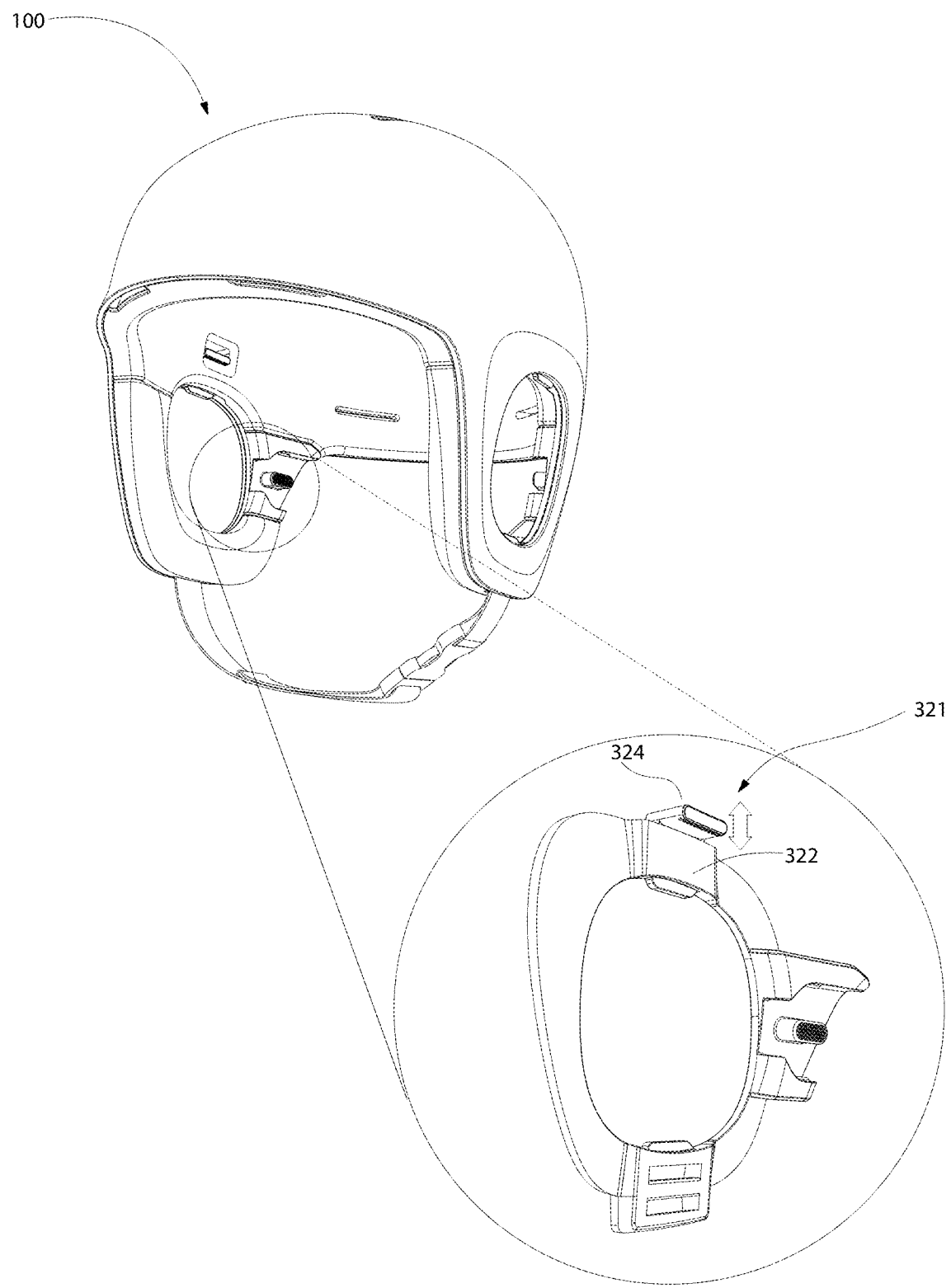
FIG. 4A is a combination perspective and detail view of a helmet with a biased locking assembly in accordance with another embodiment of the present disclosure.
Figure 4B:
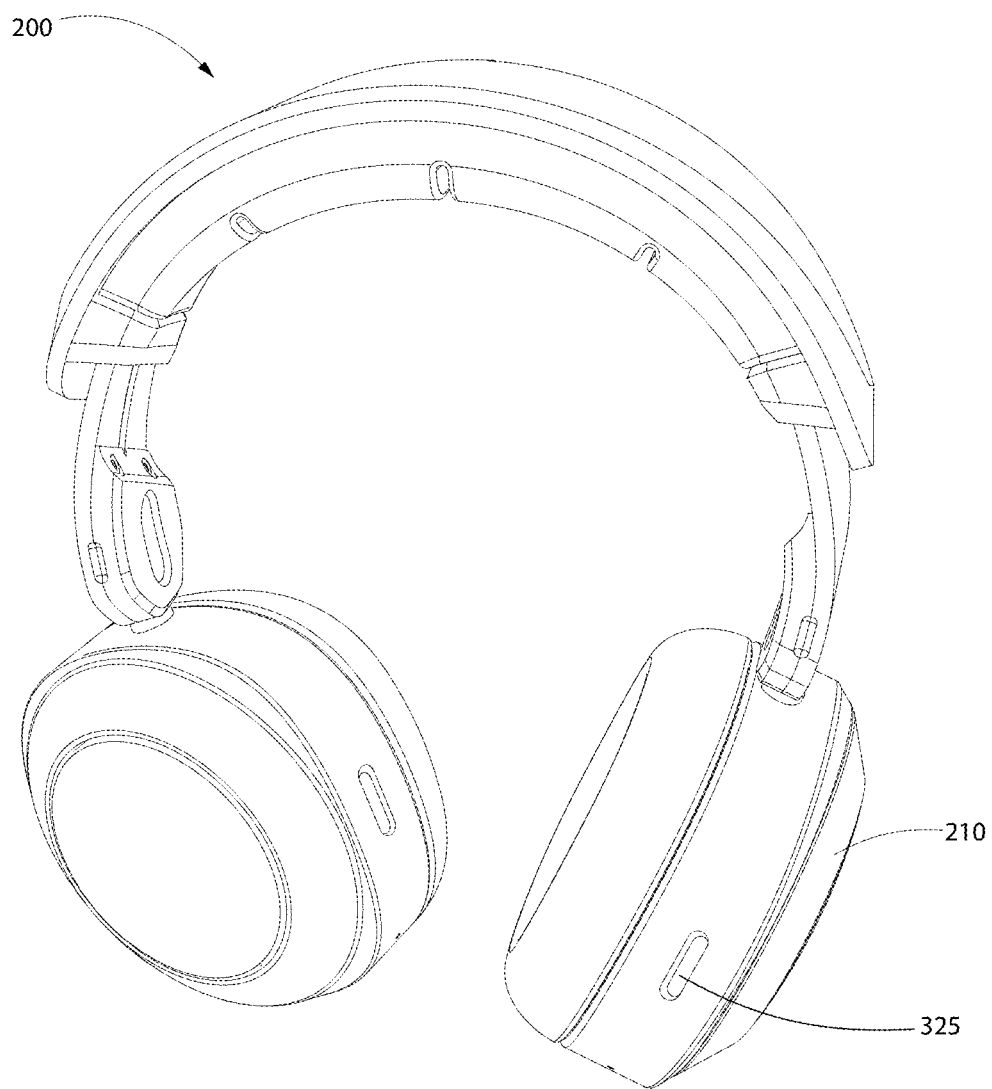
FIG. 4B is a perspective view of headphones for use with the helmet of FIG. 4A.

FIGS. 4A-4B illustrate an example of a spring biased locking assembly, in which the helmet 100 includes a male latch member 321 and the headphones include a female catch member 325. The latch member 321 may include a housing 322 that receives the biased latch in a sliding fashion, and a biasing-member, for example a spring 323 as shown in FIGS. 5A-5E. The latch member 321 may also include an arm 324 to allow for user to easily move the latch 321 between an engaged position in a disengaged position.

One or more alignment features may be used to maintain the ear cup in position relative to the ear cup receiving aperture. For example, protrusion is provided on the outer edge of the ear cup receiving aperture. A corresponding recess can be provided on the ear cup to receive the protrusion.

Figure 5A:
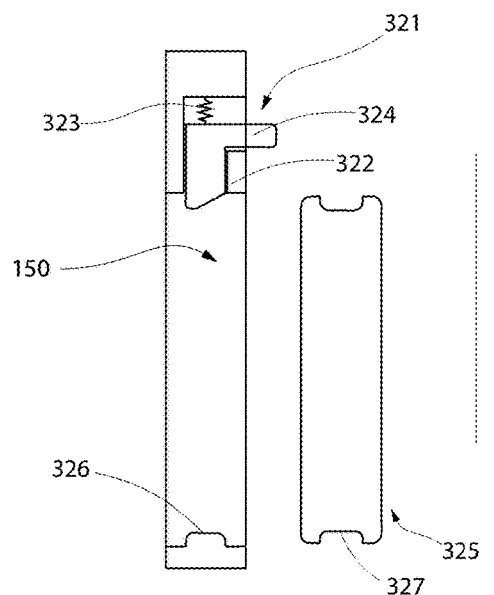
FIGS. 5A-5E are schematic views illustrating an exemplary process of attaching headphones relative to the helmet with a spring locking assembly.
Figure 5B:
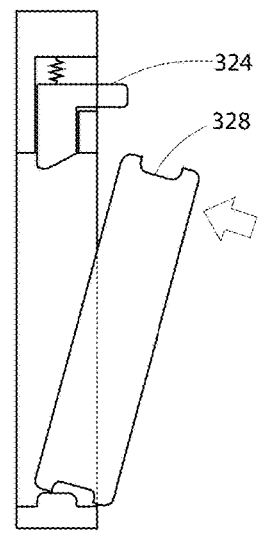
Figure 5C:
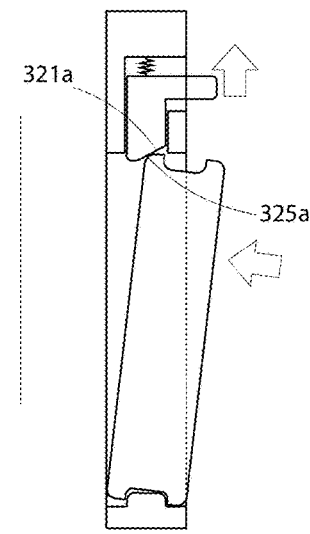
Figure 5D:
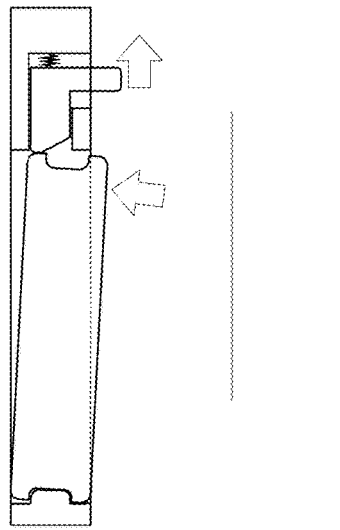
Figure 5E:
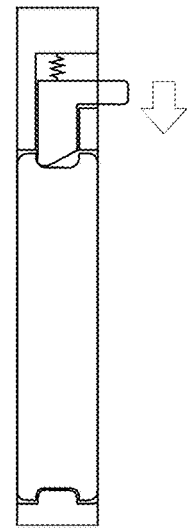

FIGS. 5A-5E illustrate use of a spring biased locking assembly according to the present disclosure. In FIG. 5A, attaching headphones relative to the helmet 100 begins with positioning a male mating member 321 relative to a female mating member 325. In FIG. 5B, female member 325 is positioned partly within protrusion 326 of male member 321 such that a recess 327 of the female member 325 is abutted against protrusion 326 of the male member 321. In FIGS. 5C and 5D an upper portion of female member 325 is urged toward the locked position. The male member 321 and female member 325 can include abutment surfaces 321a, 325a to allow for the female member 325 to slide into the locked position without manually lifting the arm 324. The abutment surfaces 321a, 325a may include one or more angled and/or rounded edges. In this manner, pressing the female member 325 into the recess 328 of the male member 321 engages respective surfaces in a manner that the male member 321 is automatically lifted into a disengaged position. In FIG. 5E, the male member 321 is positioned fully within the recess 328 of the female member 325 such that the latch is received within the catch. The female member 325 is maintained in this locked position relative to the male member via the biased latch 321.

The female member 325 can be released from the male member 321 by manually lifting the arm 324, thereby upwardly moving the latch out of the catch from the position shown in FIG. 5E. The process of removing ear cup 210 relative to the ear cup receiving aperture 150 can proceed in an opposite manner as the method of installation previously described, i.e. from FIG. 5E, to FIG. 5D, and so forth. As the ear cup 210 extends through the ear cup receiving aperture 150, the user can press against the outer edge of the ear cup 210 to move the ear cup 210 into the position shown in FIG. 5D. Alternatively or additionally, the user can pull on a portion of the headphones located within the helmet 100 (e.g. a leg) to remove the ear cup 210 from the ear cup receiving aperture 150.

Yet another embodiment of a locking assembly according to the present disclosure is a rotational locking assembly. A rotational locking assembly can include one or more rotational latch members and one or more fixed catch members. Corresponding mating features, such as protrusions and recesses can further assist in aligning the headphones and helmet relative to one another so that the headphones can be placed in a locked position with the rotational locking assembly.

Figure 6A:
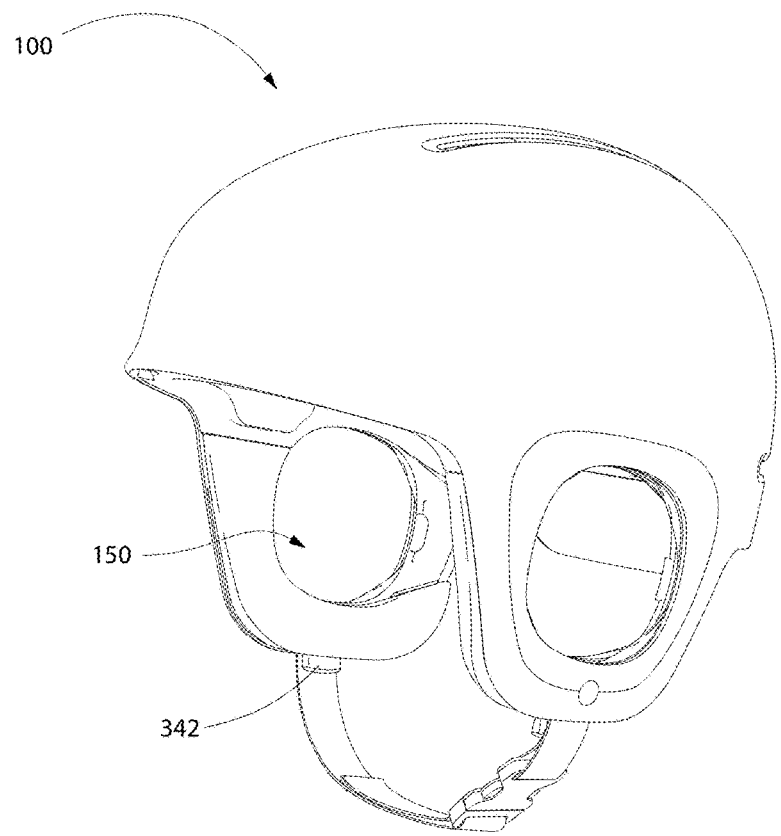
FIG. 6A is a perspective view of a helmet with a rotational locking assembly in accordance with another embodiment of the present disclosure.

FIGS. 6A-6D illustrate an example of a rotational locking assembly 340, in which the helmet 100 includes a male latch member 341 and the headphones include a female catch member 340. With reference to FIG. 6A, the helmet 100 is shown with the latch in a disengaged position. In the disengaged position, mating members of the latch are located within the helmet 100 that define a housing of the latch member 341 through which the latch member 341 rotates within. The latch member 341 includes an arm to allow for the user to move the latch between the disengaged, unlocked position and the engaged, locked position.

Figure 6B:
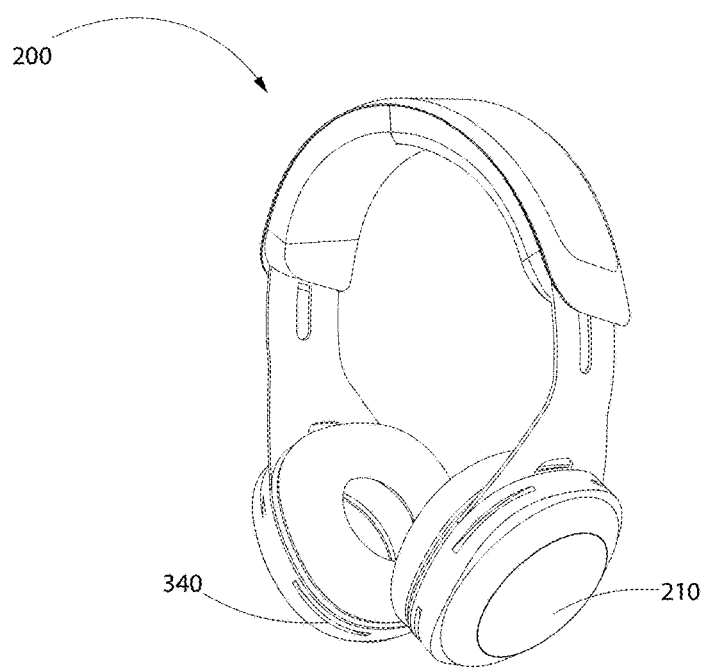
FIG. 6B is a perspective view of headphones for use with the helmet of FIG. 6A.
Figure 6C:
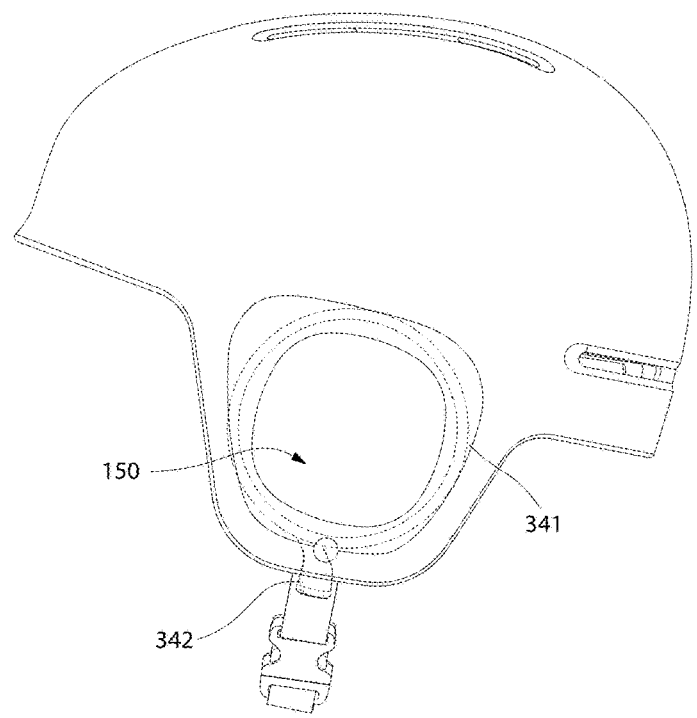
FIG. 6C is a side view of the helmet of FIG. 6A showing the rotational locking assembly in an unlocked position.
Figure 6D:
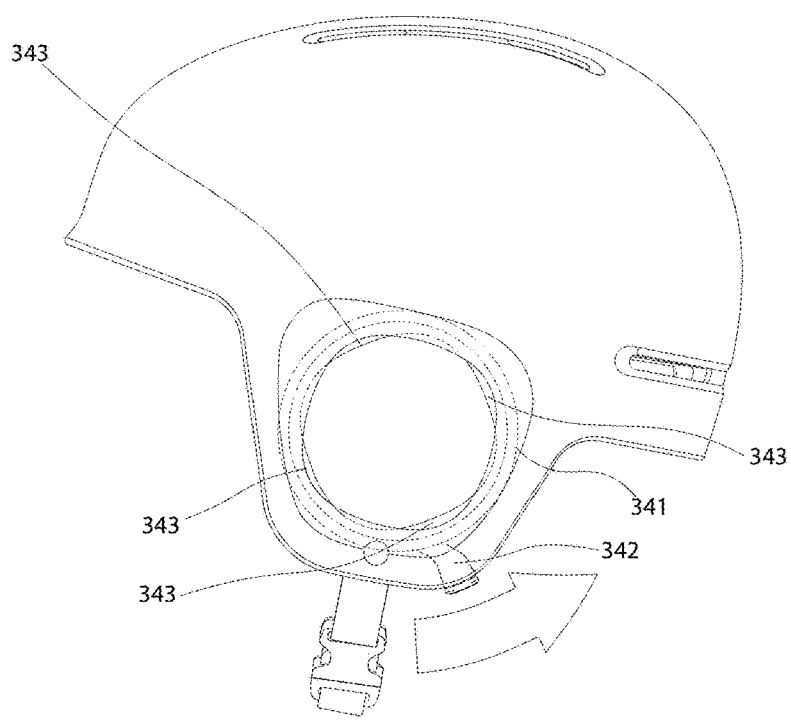
FIG. 6D is another side view of the helmet of FIG. 6A showing the rotational locking assembly in a locked position.

FIG. 6B illustrates headphones with female catch members (e.g. recesses) that receive corresponding latch member 341 when the latch 341 is moved into the locked position. FIGS. 6C and 6D shows the helmet 100 without headphones, and an outline of the (hidden) latch member 341 located within the helmet 100 in broken lines. FIG. 6C shows the rotational locking assembly in a disengaged, unlocked position. As can be seen, the male latch member 341 is not visible through the ear cup receiving aperture 150 (i.e. the latch member is disposed fully within the helmet 100). In FIG. 6D, the arm 342 is rotated rearwardly such that the latch 341 is moved into the engaged, locked position thereby exposing one or more portions of the latch member 341 that can be received by the one or more corresponding catch members. In this particular example, the latch member 341 exposes four edge features 343 from the edge of the ear cup aperture 150. When the ear cup 210 is located through the ear cup aperture 150, the rotational latch member 341 can be rotated into the engaged, locked position where the edge features mate in a locked manner with the corresponding catch members.

Figure 7A:
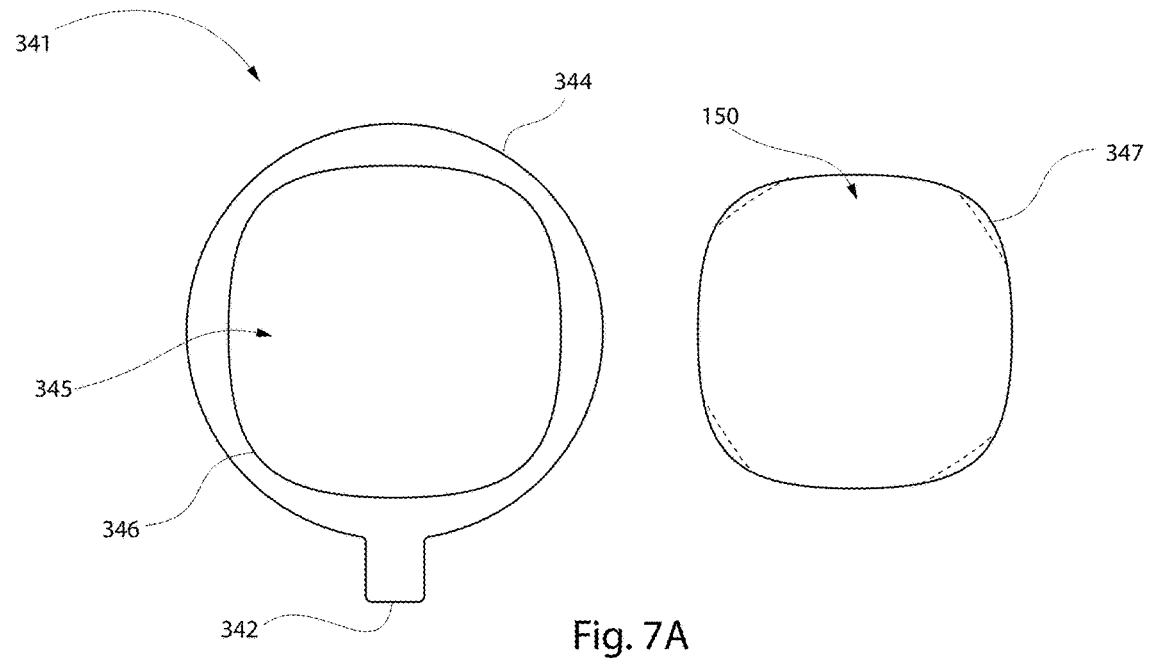
FIGS. 7A-7C are schematic views illustrating a process of operating the rotational locking assembly of FIG. 6A.
Figure 7B:
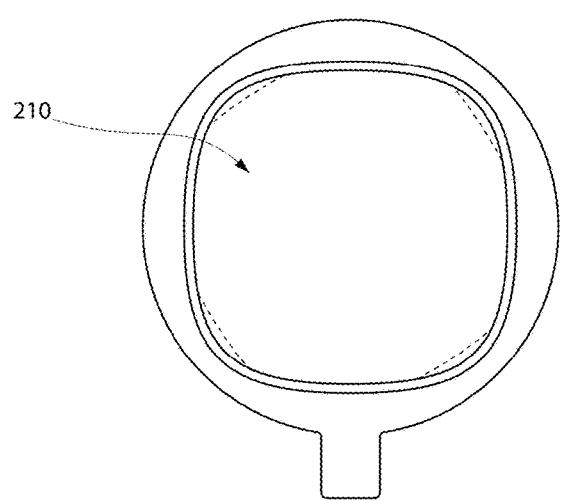
Figure 7C:
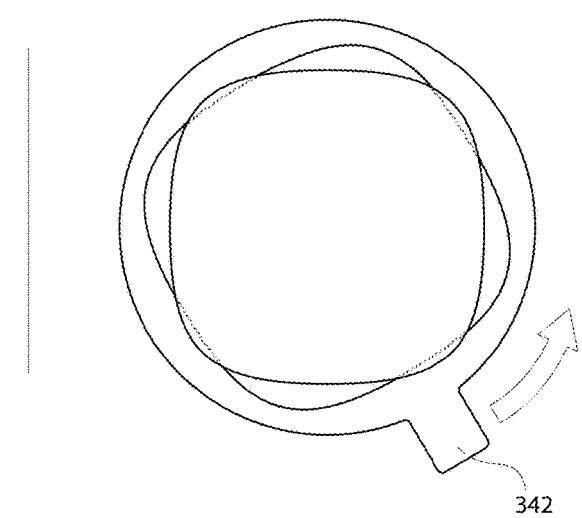

FIGS. 7A-7C illustrate the principle of a rotational locking assembly according to the present disclosure. As shown in FIG. 7A, the male latch member 341 can be a flat disk with a rounded (e.g. circular) outer periphery 344 and an inner aperture 345 defined by an inner edge 346. The male latch member 341 may be received within a male latch housing (not shown) located within the helmet, for example between an outer shell and inner shell of the helmet. The male latch 341 can define a mating edge 347 that slidably receives the outer circumference of the female catch member 340. In some embodiments, male latch housing and the outer circumference of the male latch 341 can have a frictional fit that requires a threshold force for the user to overcome in order to rotate the latch about the latch housing. In this way, the male latch member 341 can avoid from being inadvertently moved between locked and unlocked positions.

The female catch member 340 can be one or more recesses within a peripheral housing. For example, as illustrated in FIGS. 6B, one or more recesses can be disposed within an outer edge of an ear cup 210 of the headphones. The one or more recesses 340 can define a mating edge that mirrors an engagement edge of the latch member 341.

FIG. 7B depicts the ear cup 210 disposed within the ear cup aperture 150, the rotational locking assembly in a disengaged, unlocked position. From this position, the arm 342 of the latch member 341 can be rotated into the engaged, locked position as shown in FIG. 7C. In the engaged, locked position, engaging edges 347 of the latch member 341 are received within the respective recesses of the catch member such that the ear cup 210 is secured relative to the helmet 100.

The female member 340 can be released from the male member 341 by rotating the arm 342 from the locked position into the unlocked position, thereby moving each of the respective engaging edges 347 out of the respective recesses 340 of the catch member. The process of removing ear cup 210 relative to the ear cup receiving aperture 150 can proceed in an opposite manner as the method of installation previously described, i.e. from FIG. 7C to FIG. 7B, and then to FIG. 7A. As the ear cup 210 extends through the ear cup receiving aperture 150, the user can press against the outer edge of the ear cup 210 to move the ear cup 210 out of the ear cup receiving aperture 150. Alternatively or additionally, the user can pull on a portion of the headphones located within the helmet (e.g. a leg) to remove the ear cup 210 from the ear cup receiving aperture 150.

According to another embodiment of the present disclosure, the headphones may be releasably detachable from the helmet using other rotational locking assemblies. Another example of a rotational lock assembly can allow for rotational locking of the headphones relative to the helmet by rotation of the entire headphones relative to the helmet. In this example of a rotational locking assembly, the helmet and headphones can include one or more male latch members (e.g. protrusion) and female catch member (e.g. recess). Respective latch and catch members can be located on the periphery of the ear cup and the edge of the ear cup aperture.

Figure 8C:
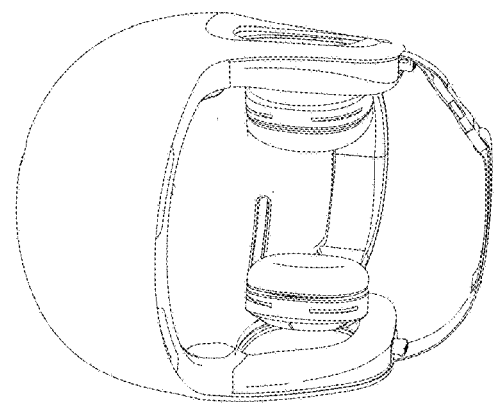
FIGS. 8A-8F are perspective views illustrating a process of attaching headphones to a helmet with a rotational locking assembly in accordance with an embodiment of the present disclosure.
Figure 8B:
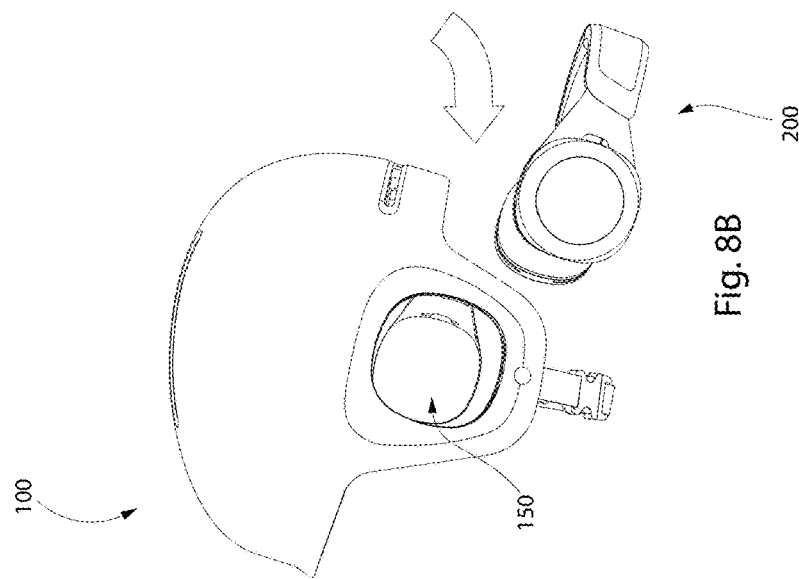
Figure 8A:
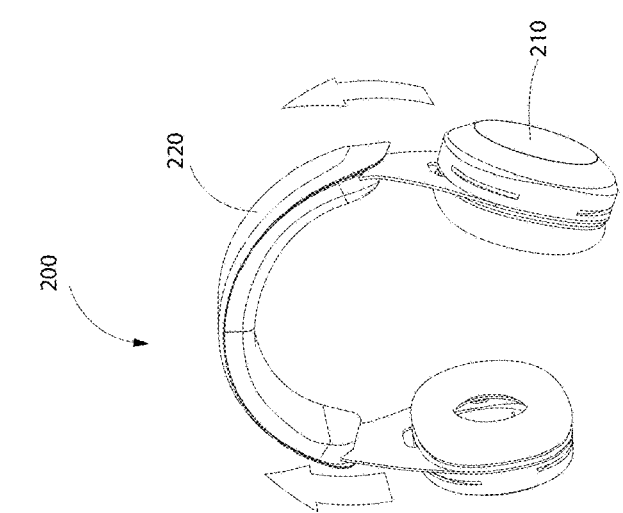
Figure 8F:
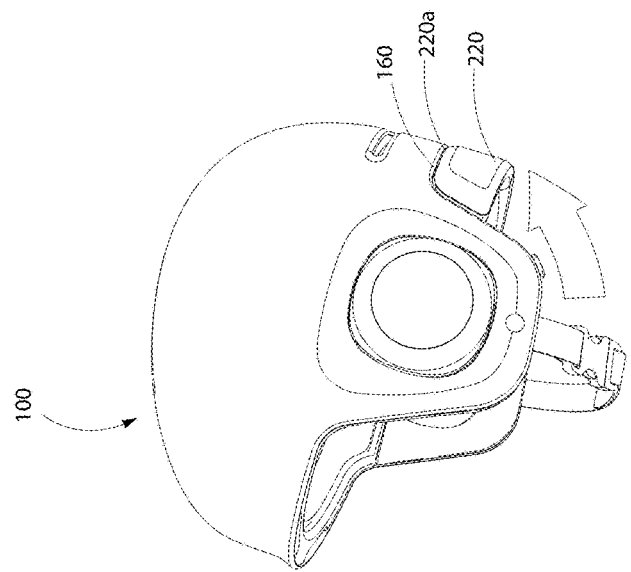
Figure 8E:
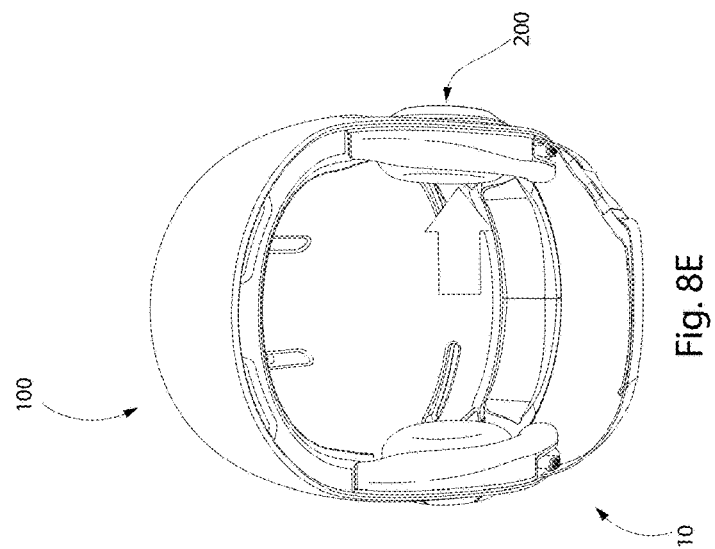
Figure 8D:
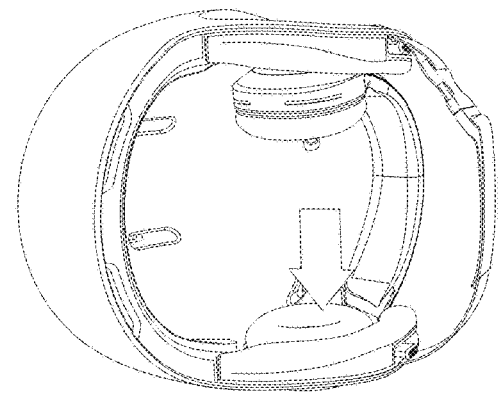

FIGS. 8A-8F illustrate one particular arrangement for mating the headphones 200 and helmet 100 via a rotational locking assembly. According to FIG. 8A, the headphones 200 can be compressed to their minimum size by sliding the ear cups 210 towards the head band 220. Subsequently, the ear cups 210 of the headphones 200 can be positioned toward the ear cup apertures 150 of the helmet 100 as shown in FIG. 8B and 8C. FIGS. 8D and 8E subsequently shows individual ear cups 210 being disposed through a corresponding ear cup aperture 150 of the helmet 100. The rotational locking assembly can be positioned from a disengaged, unlocked position into the engaged, locked position by rotating the headphones as shown in FIG. 8F.

The male and female rotational locking members may have a frictional fit in order to maintain the headphones in the locked position during use. Similarly, the helmet 100 and headphones can include additional frictional and/or alignment features to maintain the headphones. For example, the helmet 100 can include a recess for receiving portions of the headphones in the locked position. FIG. 8F illustrates that the headphones and helmet 100 can have mating edges 160, 220a that assist in alignment and improve aesthetics by providing a seamless appearance. Specifically, the headband 220 includes a contoured edge 220a that follows a corresponding contoured edge 160 at the rear of the helmet 100.

Figure 9A:
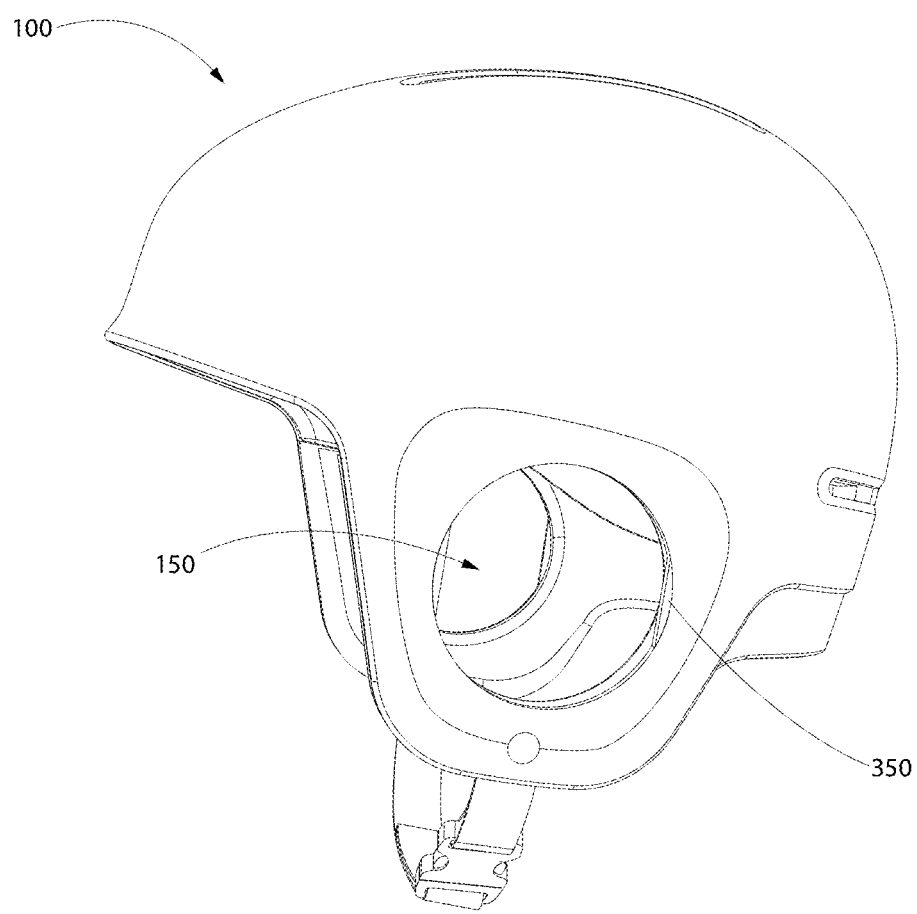
FIG. 9A is a perspective and detail view of a helmet with the rotational locking assembly shown in FIGS. 8A-8F.
Figure 9B:
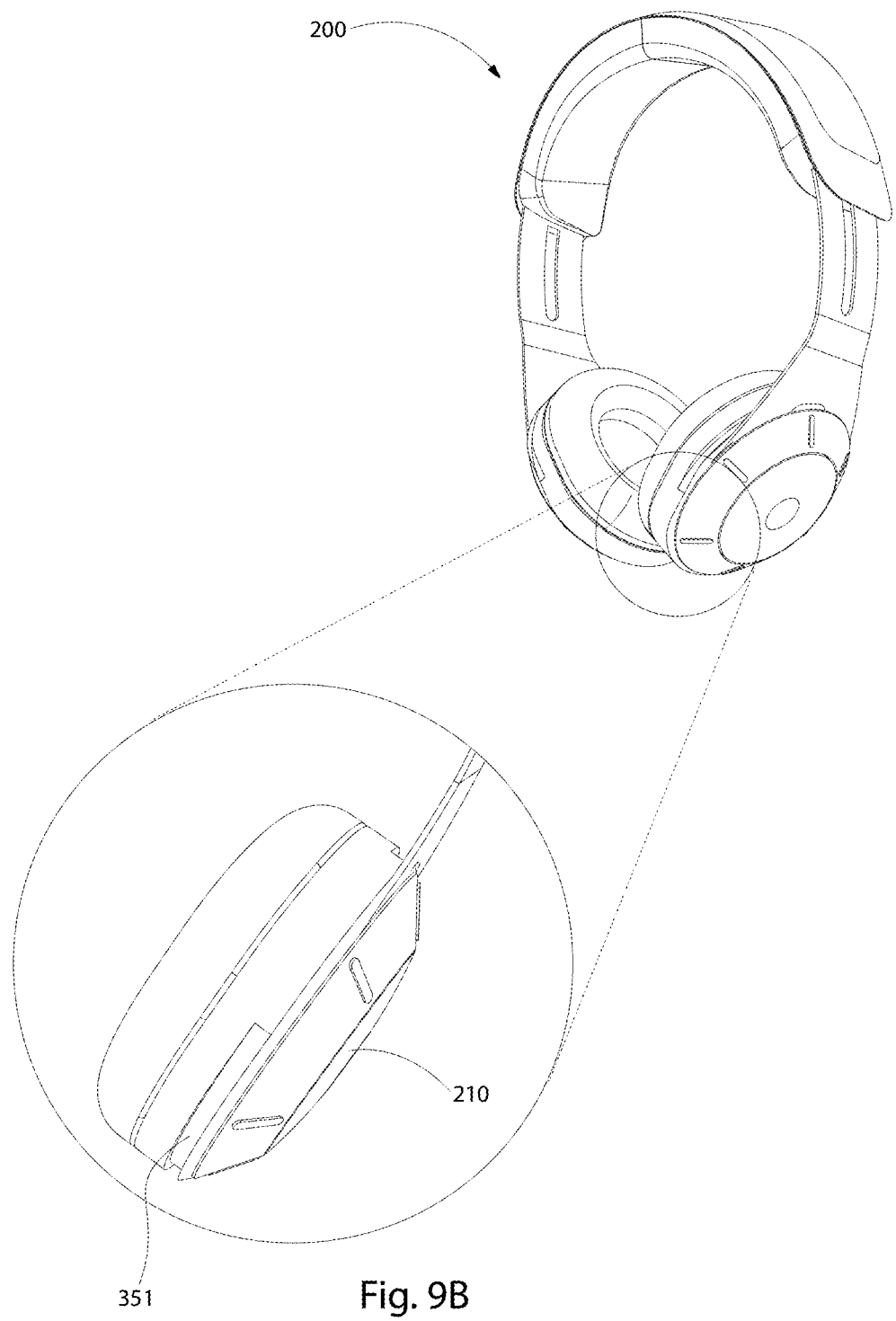
FIG. 9B is a perspective view of headphones for use with the helmet of FIG. 9A.

FIGS. 9A and 9B illustrate another example of a rotational lock assembly where the edge of the ear cup aperture 150 includes one or more protrusions 350, and an edge of the ear cup 210 includes corresponding recesses 351 that are configured to rotationally receive the one or more protrusions 350 therein. The headphones can be removably attachable to the helmet 100 by rotating the ear cups 210 within the ear cup apertures 150.

Figure 10A:
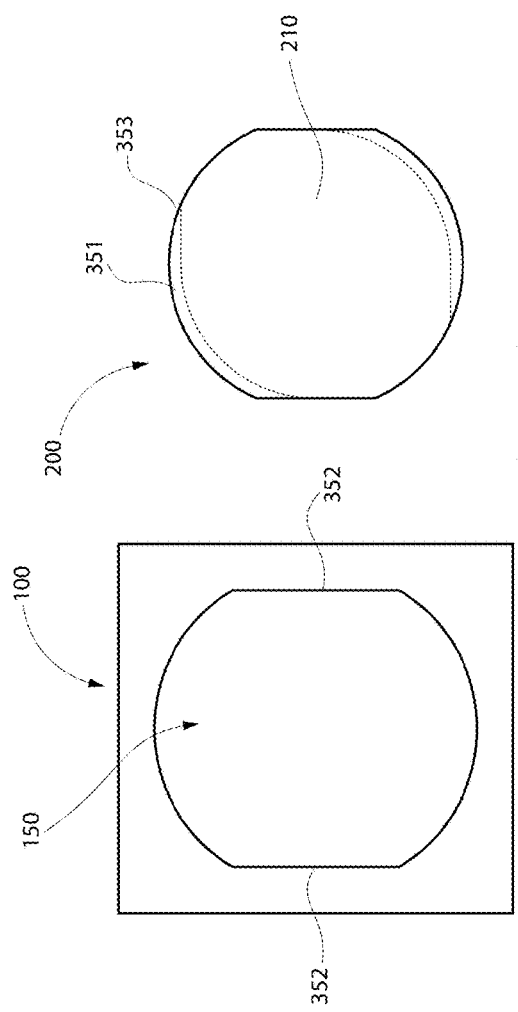
FIGS. 10A-10D are schematic views illustrating a process of attaching headphones to a helmet with a rotational locking assembly in accordance with an embodiment of the present disclosure.
Figure 10D:
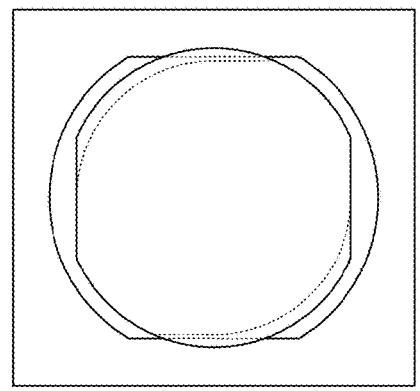

FIGS. 10A-10D schematically demonstrate the principle used in the rotational lock assembly depicted in FIGS. 9A and 9B. As shown in FIG. 10A, the male latch member 350 is defined by an edge 352 of the ear cup aperture 150. The female catch member can be defined by one or more recesses 351 disposed within an outer edge 353 of an ear cup 210 of the headphones. The one or more recesses 351 can define a mating edge that mirrors an engagement edge of the male edge 352.

Figure 10C:
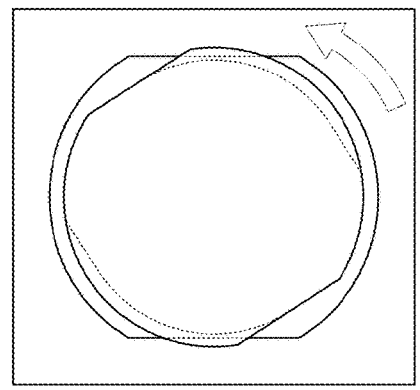
Figure 10B:
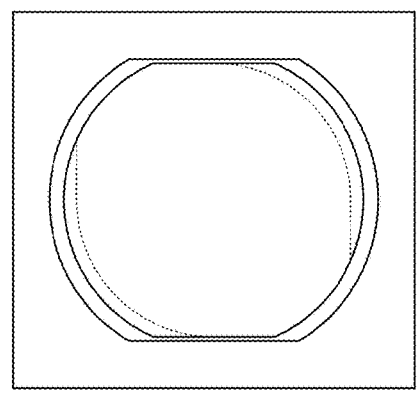

FIG. 10B depicts the ear cup 210 disposed within the ear cup aperture 150, where the rotational locking assembly is in a disengaged, unlocked position. From this position, the ear cup 210 can be rotated into the engaged, locked position as shown in FIG. 10C. In the engaged, locked position of FIG. 10D, engaging edges 352 of the latch member are received within the respective recesses 351 of the catch member such that the ear cup 210 is secured relative to the helmet 100.

The female member can be released from the male member by rotating the entire headphones 200 from the locked position into the unlocked position, thereby moving each of the respective engaging edges 352 out of the respective recesses 351 of the catch member. The process of removing ear cup 210 relative to the ear cup receiving aperture 150 can proceed in an opposite manner as the method of installation previously described, i.e. from FIG. 10D to FIG. 10C, and so forth as the ear cup 210 extends through the ear cup 210 receiving aperture 150, the user can press against the outer edge of the ear cup 210 to move the ear cup 210 out of the ear cup receiving aperture 150. Alternatively or additionally, the user can pull on a portion of the headphones located within the helmet (e.g. a leg) to remove the ear cup 210 from the ear cup receiving aperture 150.

Figure 11A:
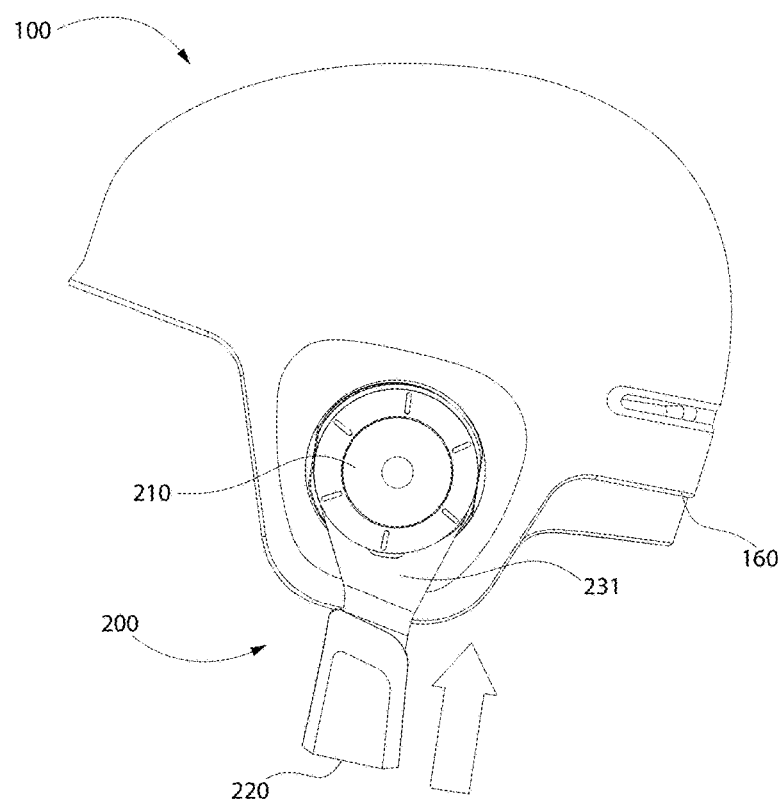
FIG. 11A is a side view of the helmet and headphones of FIGS. 9A-9B showing the rotational locking assembly in an unlocked position.
Figure 11B:
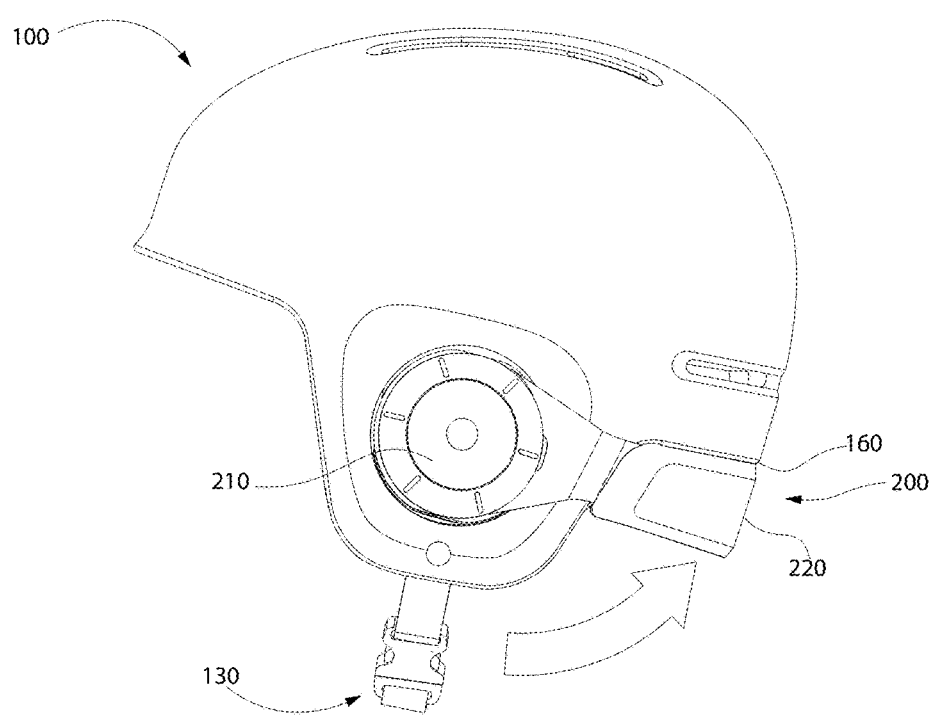
FIG. 11B is another side view of the helmet and headphones of FIGS. 9A-9B showing the rotational locking assembly in a locked position.

FIGS. 11A-11B illustrate one particular arrangement for mating the headphones and helmet 100 via a rotational locking assembly. According to FIG. 11A, the ear cups 210 of the headphones can be inserted into the respective ear cup apertures 150 of the helmet 100. For example, in an unlocked position, the ear cup 210 may fit within the ear cup aperture 150 in a position where the headband 220 of the headphones 200 is oriented downwardly, towards the chinstrap of the helmet 100. The headphones 200 can be rotationally locked into a fixed position by rotating the entire headphones 200 about the ear cup aperture 150 such that respective male and female members located on the ear cups 210 and edge of the ear cup apertures 150 mate. For example, the headphones can be rotated towards the rear of the helmet 100, and in a final position, the respective male and female members are fixed relative to one another. In the engaged, locked position the headband 220 and legs 231 may be located in a horizontal or substantially horizontal position, which is described in further detail herein with reference to FIGS. 24A-24D. In the engaged, locked position shown in FIG. 11B, the headband 220 of the headphones may abut a rear edge 160 of the helmet 100.

The male and female rotational locking members may have a frictional fit in order to maintain the headphones in the locked position during use. Similarly, the helmet 100 and headphones can include additional frictional and/or alignment features to maintain the headphones. For example, the helmet 100 can include a recess for receiving portions of the headphones in the locked position. FIG. 11A provides an example of a frictional and/or alignment feature, where the rear of the helmet 100 includes a recess for receiving the headband 220 in the locked position. FIG. 11B illustrates that the headphones and helmet 100 can have mating edges that assist in alignment and improve aesthetics by providing a seamless appearance. Specifically, the headband 220 includes a contoured edge that follows a corresponding contoured edge at the rear of the helmet 100.

In another embodiment according to the present disclosure, a locking assembly can include a sliding locking assembly. A sliding locking assembly can include one or more sliding latch members and one or more catch members. Corresponding mating features, such as protrusions and recesses can further assist in aligning the headphones and helmet relative to one another so that the headphones can be placed in a locked position with the sliding locking assembly.

Figure 12A:
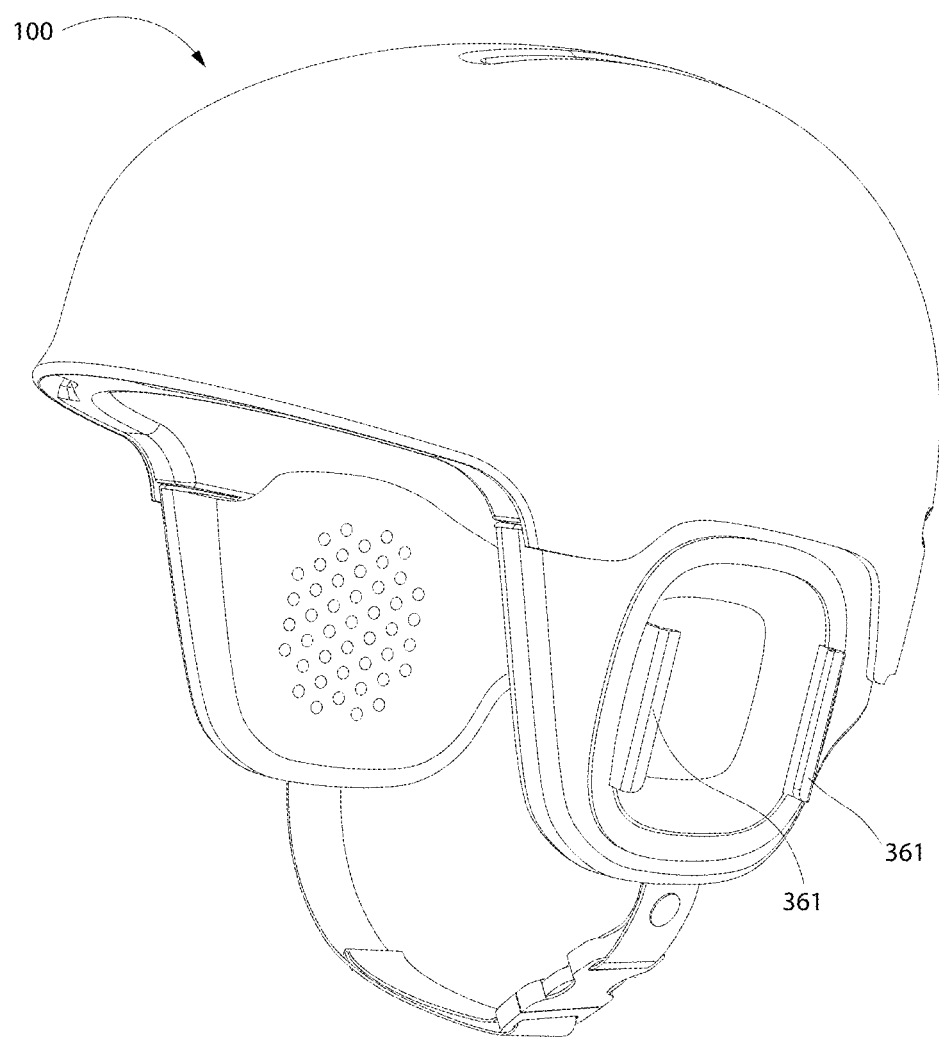
FIG. 12A is a perspective view of a helmet with a sliding locking assembly in accordance with another embodiment of the present disclosure.
Figure 12B:
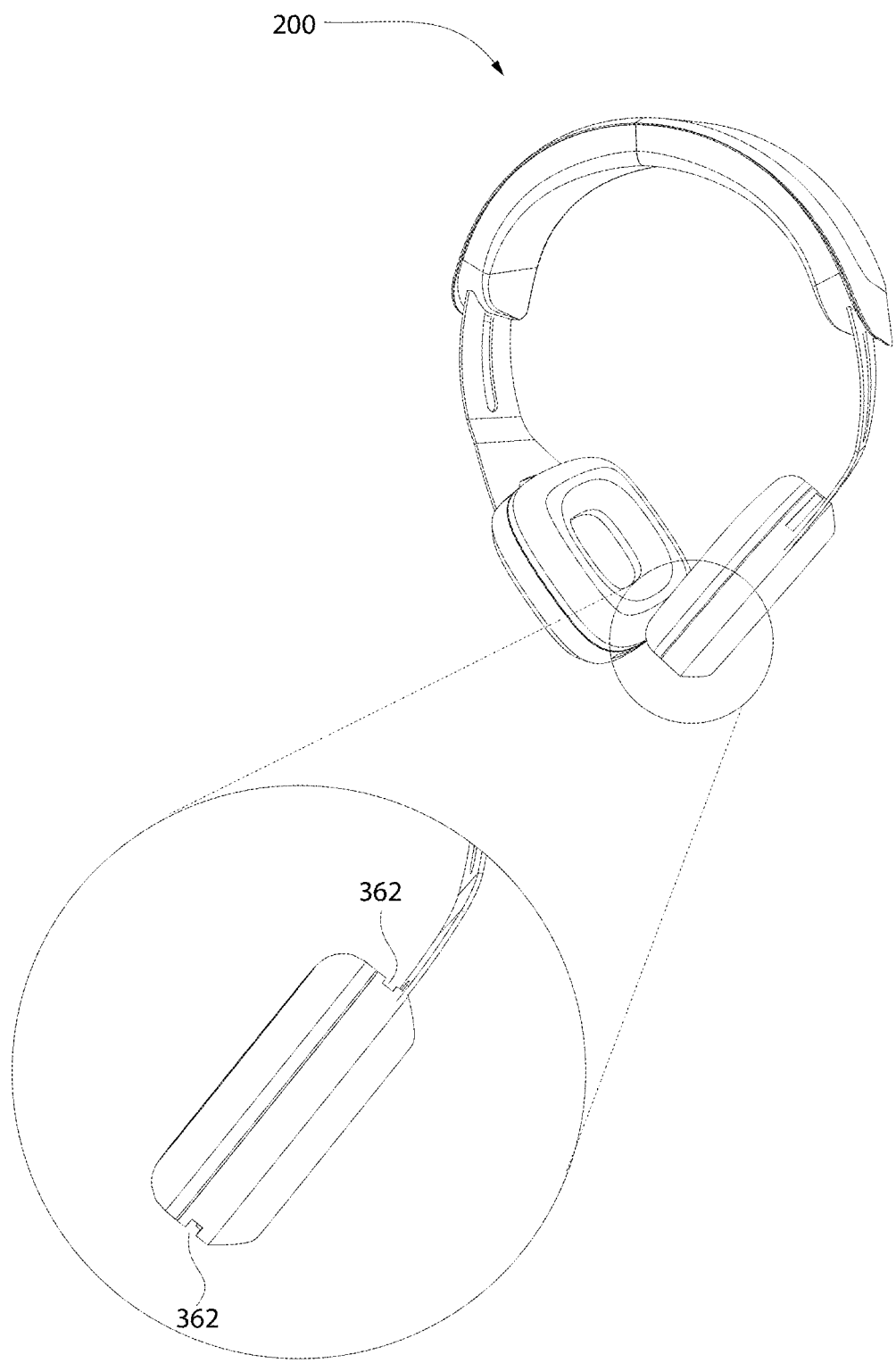
FIG. 12B is a combination perspective and detail view of headphones for use with the helmet of FIG. 12A.

FIGS. 12A-12B illustrate an example of a sliding locking assembly, in which the helmet 100 includes male latch members 361 and the headphones include female catch members 362. With reference to FIG. 12A, the male latch members 361 are embodied as a pair of parallel, linear protrusions that are fixed adjacent to each ear cup aperture 150. FIG. 12B illustrates headphones 200 with female catch members 362 (e.g. recesses) that receive the corresponding latch members 361 when the latch members are slid into the catch members 362, thereby placing the sliding locking assembly in an engaged, locked position.

FIGS. 13A-13D schematically demonstrate the principle used in the sliding lock assembly 360 depicted in FIGS. 12A and 12B. As shown in FIG. 13A, the male latch member 361 is defined by one or more linear protrusions (e.g. two protrusions) located at an edge of the ear cup aperture 150. The protrusions can include an extension piece 363, which extends away from the ear cup aperture 150, and a linear engagement edge 364 that is configured to engage a female catch member 362. The female catch member 362 can be defined by one or more recesses 365 (e.g. two recesses) disposed within an outer edge of an ear cup 210 of the headphones. The one or more recesses 365 can define a mating edge that mirrors an engagement edge of the latch member 361. In this example, the ear cup 210 includes two correspondingly linear recesses 365. The male latch member 361 and female catch member 362 may have flexible mating features that interlock with one another in a frictional manner (e.g. "snap-fit") in order to maintain the sliding locking assembly in an engaged, locked position.

FIG. 13B depicts the recesses of an ear cup 210 in a linearly aligned position with the with the latch member of the ear cup aperture 150. From this position, the latch member can be slid into the engaged, locked position as shown in FIG. 13C. FIG. 13D is a cross-sectional view showing the sliding locking assembly in the engaged, locked position of FIG. 13C. FIG. 13E illustrates that an inner portion of the ear cup can be compressed in order to place the ear cup in the locked position in FIG. 13D.

The female member can be released from the male member by sliding the ear cups 210 from the locked position into the unlocked position, thereby moving each of the respective engagement edges out of the respective recesses of the catch member. The process of removing the ear cup 210 relative to the ear cup receiving aperture 150 can proceed in an opposite manner as the method of installation previously described, i.e. from FIG. 13C to FIG. 13B, and so forth.

Figure 14A:
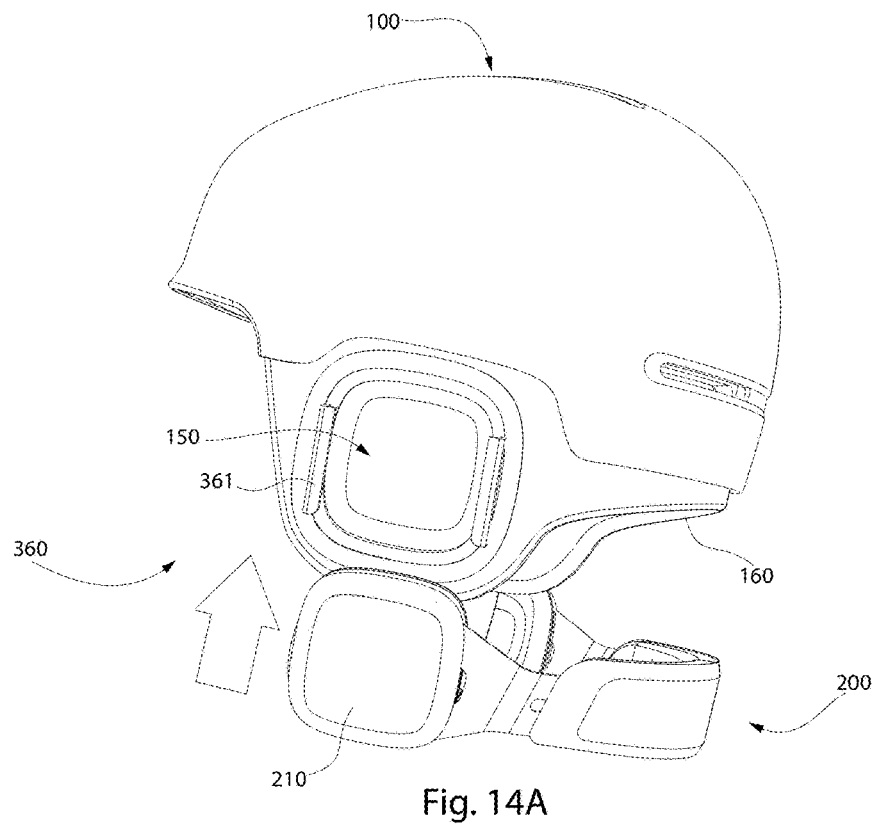
FIG. 14A is a side view of the helmet and headphones of FIGS. 12A-12B showing the sliding locking assembly in an unlocked position.
Figure 14B:
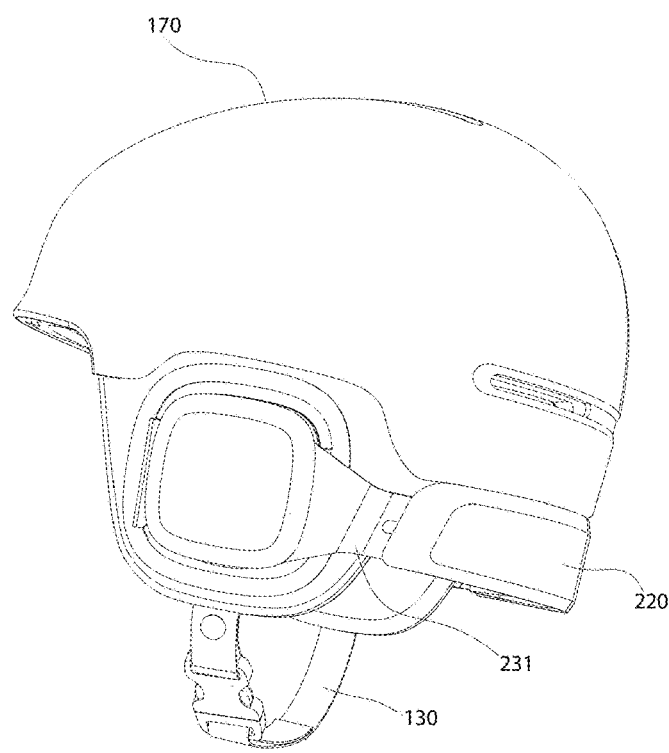
FIG. 14B is another side view of the helmet and headphones of FIGS. 12A-12B showing the sliding locking assembly in a locked position.

FIGS. 14A-14B illustrate one particular arrangement for mating the headphones and helmet 100 via a sliding locking assembly 360. According to FIG. 14A, the ear cups 210 of the headphones 200 can be slid toward the respective male latch members 361 located adjacent the ear cup apertures 150 of the helmet 100. In one particular example, the headphones 200 and helmet 100 may mate by sliding the headphones 200 in a vertical direction, i.e. in a direction starting from the chinstrap and upwardly toward the crown 170 of the helmet 100. In the engaged, locked position of FIG. 14B, the headband 220 and legs 231 may be located in a horizontal or substantially horizontal position. In the engaged, locked position shown in FIG. 14B, the headband 220 of the headphones may abut a rear edge 160 of the helmet 100.

According to other embodiments of the present disclosure, a headphone leg locking assembly can be used to allow for removably attaching headphones relative to a helmet. A headphone leg locking assembly can be used on its own in order to secure headphones to the helmet, or be used in addition to the above-described locking assemblies that rely on mating features disposed on the ear cups of the headphones.

Figure 15A:
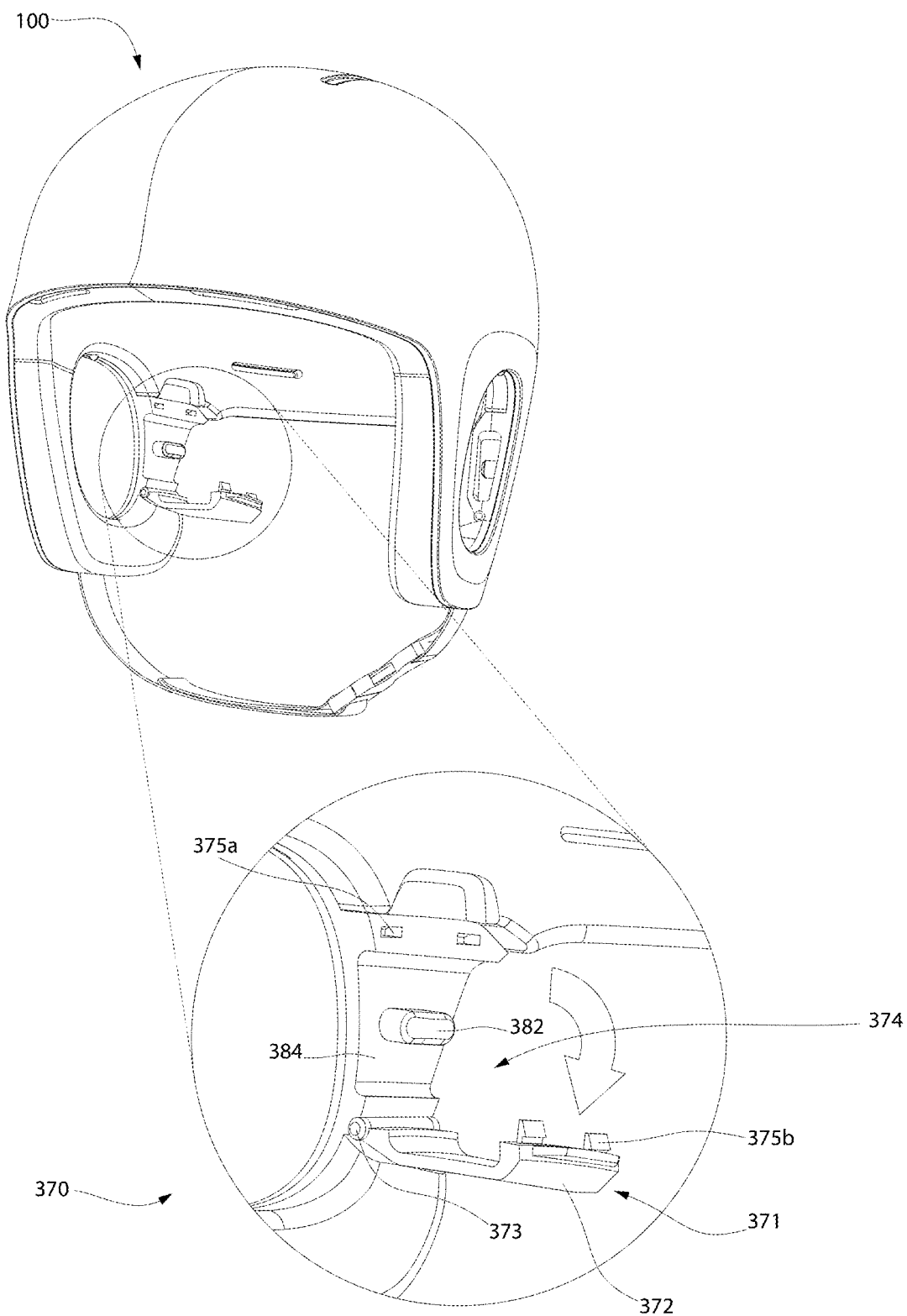
FIG. 15A is a combination perspective and detail view of a helmet with a leg locking assembly in accordance with an embodiment of the present disclosure.
Figure 15B:
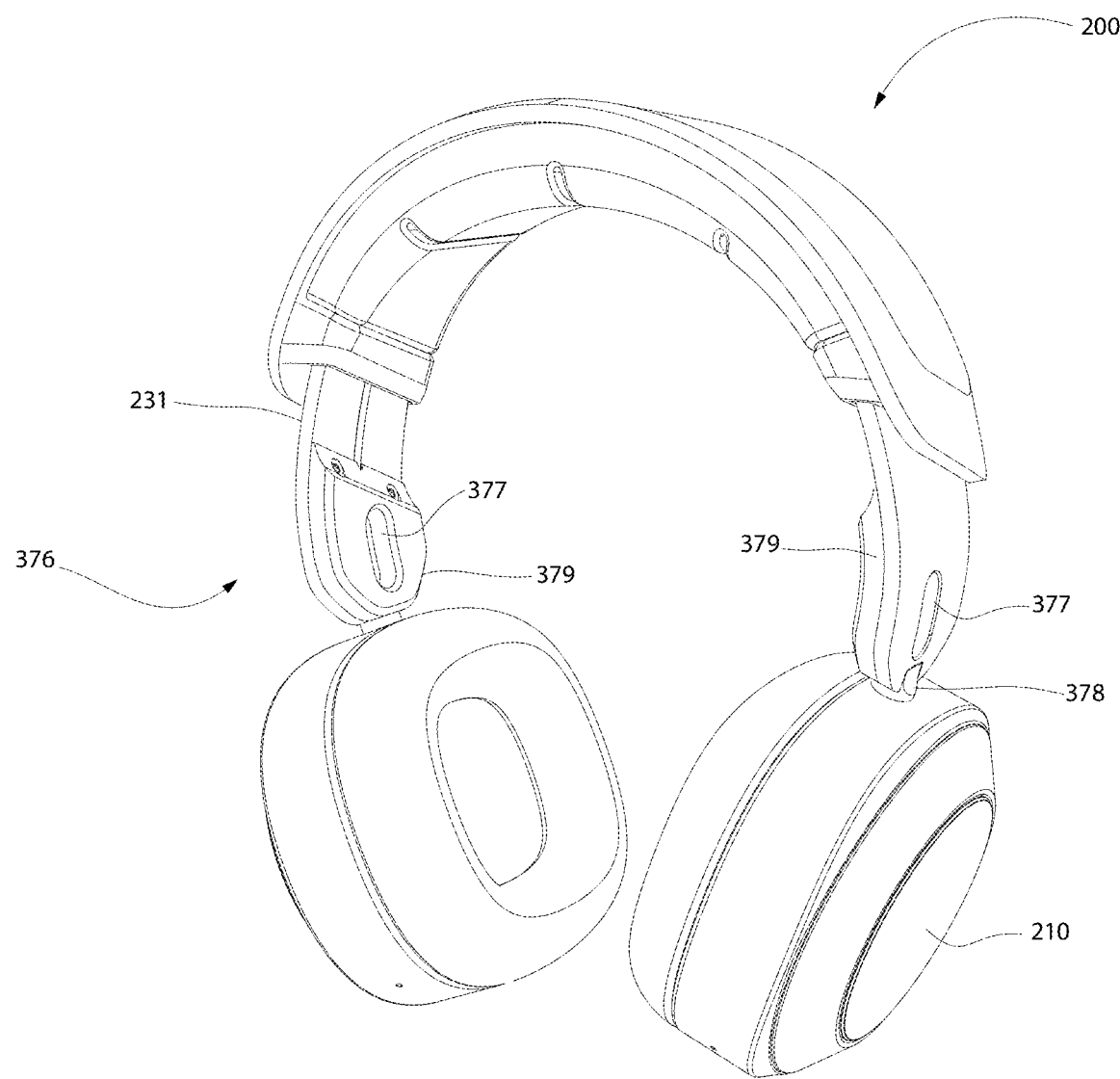
FIG. 15B is a perspective view of headphones for use with the helmet of FIG. 15A.

FIGS. 15A-15B illustrate an example of a rotational headphone leg locking assembly 370, in which the helmet 100 includes a male latch member 371 and the headphones 200 include a female catch member 376. With reference to FIG. 15A, the helmet 100 is shown with the latch in a disengaged position where the rotational latch 371 is swung open. The rotational latch 371 can be embodied by a clasp 372 that includes a hinge 373, a cavity 374 for receiving a leg 231 of the headphones 200, and locking features 375a, 375b. The rotational latch 371 can further include one or more alignment features, including a trough 384 and a protrusion 382 for aligning the leg 231 of the headphone within the rotational latch 371. The locking features 375a, 375b can include one or more hooks 375a that engage corresponding notches 375b.

FIG. 15B illustrates headphones with female catch members 377 (e.g. recesses). The catch members 377 can be disposed through legs 231 of the headphones 200. An extension 379 may be added to the legs 231 in order to increase the width of the legs 231 (e.g. where the legs 231 are made of a thin planar material). In the embodiment shown in FIG. 15B, the ear cups can rotate relative to the legs 231 via a swivel connection 378. The extension 379 can house a portion of the swivel connection 378 therein.

Figure 16A:
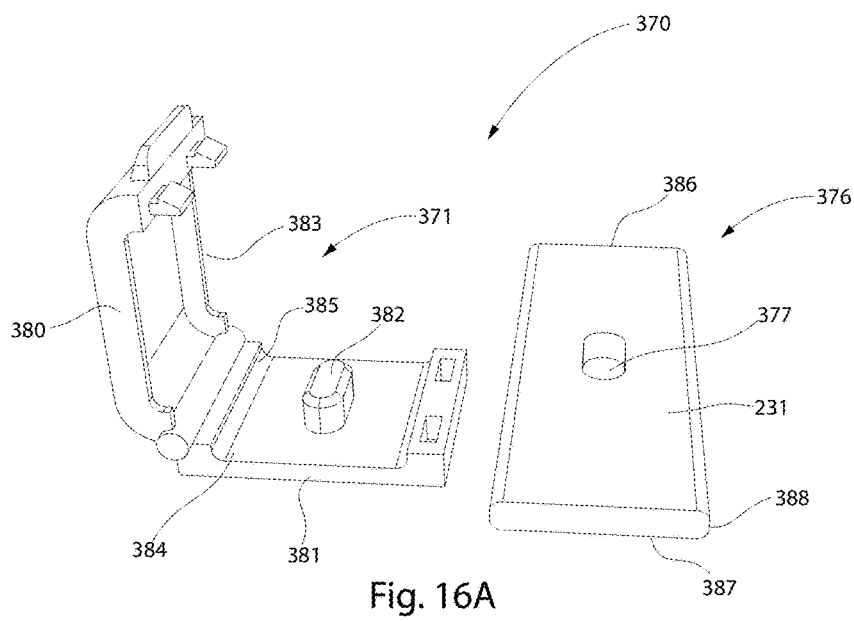
FIGS. 16A-16D are perspective views illustrating a process of attaching headphones to a leg locking assembly in accordance with an embodiment of the present disclosure.

FIGS. 16A-16E schematically demonstrate the principle used in the rotational lock assembly depicted in FIGS. 15A and 15B. As shown in FIG. 16A, the male latch member 371 can be positioned in an open state, where an outside door 380 is swung away from base member 381. The male latch member 371 can further include protrusion 382. The female catch member 376 can be defined by the leg 231 of the headphones 200, and further include in some embodiments a recess 377 that is configured to meet with the protrusion 382 of the male member 371. The male latch member 371 may include an upper surface 383 and a lower surface 384 and sidewalls 385, which abut corresponding edges and upper surface 386 and lower surface 387 of the legs 231 of the headphones 200.

Figure 16B:
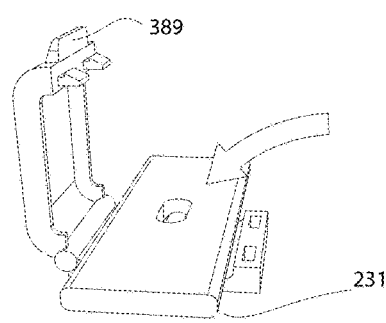
Figure 16C:
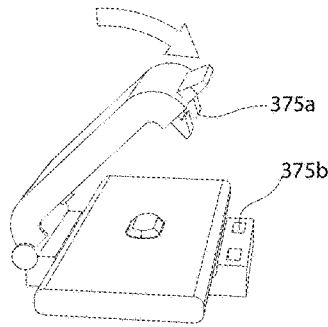
Figure 16D:
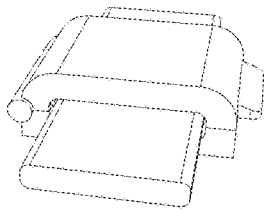
Figure 16E:
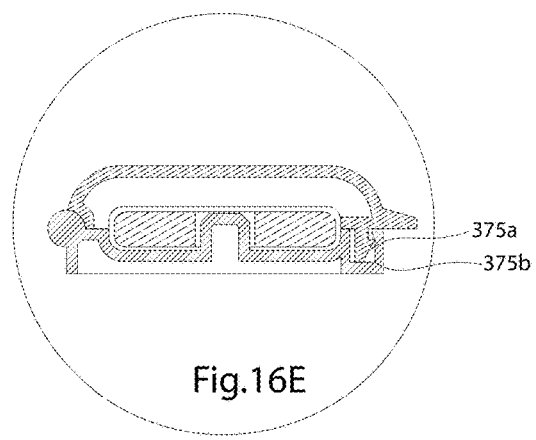
FIG. 16E is a cross-sectional view of FIG. 16D showing the headphones in a locked position.

FIG. 16B depicts the female catch member 376 (e.g. leg) being positioned towards the rotational locking assembly. From this position, the female catch member 376 can be lowered into the male latch member 371 as shown in FIG. 16C, and the door 380 of the male latch member 371 can be rotated toward a locked, engaged position. FIG. 16D shows the male latch member 371 in the engaged, locked position, where the hooks 375a have mated with the corresponding notches 375b. FIG. 16E provides a cross-sectional view of the male latch member 371 in the engaged, locked position. The hooks 375a may be made of a deformable material such that hooks 375a can create a releasably detachable snap-fit within the notches 375b.

The female member 376 can be released from the male member 371 by rotating the door 380 from the locked position into the unlocked position. A handle 389 may be provided on the door 380 to help a user grasp the door 380 for rotation. The process of removing the female member 371 can proceed in an opposite manner as the method of installation previously described, i.e. from FIG. 16D to FIG. 16C, and so forth.

FIG. 17 illustrates another example of a headphone leg locking assembly, in which the helmet (not shown) includes a male latch member 391 and the leg 231 serves as a female catch member 399. The male latch member 391 can be a deformable docking frame 392 that includes one or more deformable arms 393 that act as cantilevers. The one or more deformable arms 393 may deform (e.g. bend) outwardly in order to receive and retain a leg 231 of the headphones 200 within a cavity 394 defined by the space within each arm 393. In order to improve deformation, the deformable docking frame 392 can have weakened portions 395 (e.g. apertures) to improve deformability. The male member 391 can include engagement edges 396 for retaining a leg 231 of the headphones 200 in a locked position. The engagement edges 396 can further have an alignment features, such as an alignment surface 397 (e.g. a beveled or rounded edge), which can assist in urging the arms 393 into a locked position. Each of the one or more deformable arms 393 can include an extended edge 398 that assists a user in the cantilever action of the arm 393. For example, the extended edge 398 can improve grip and decrease the forces necessary to deform each arm 393.

Figure 18A:
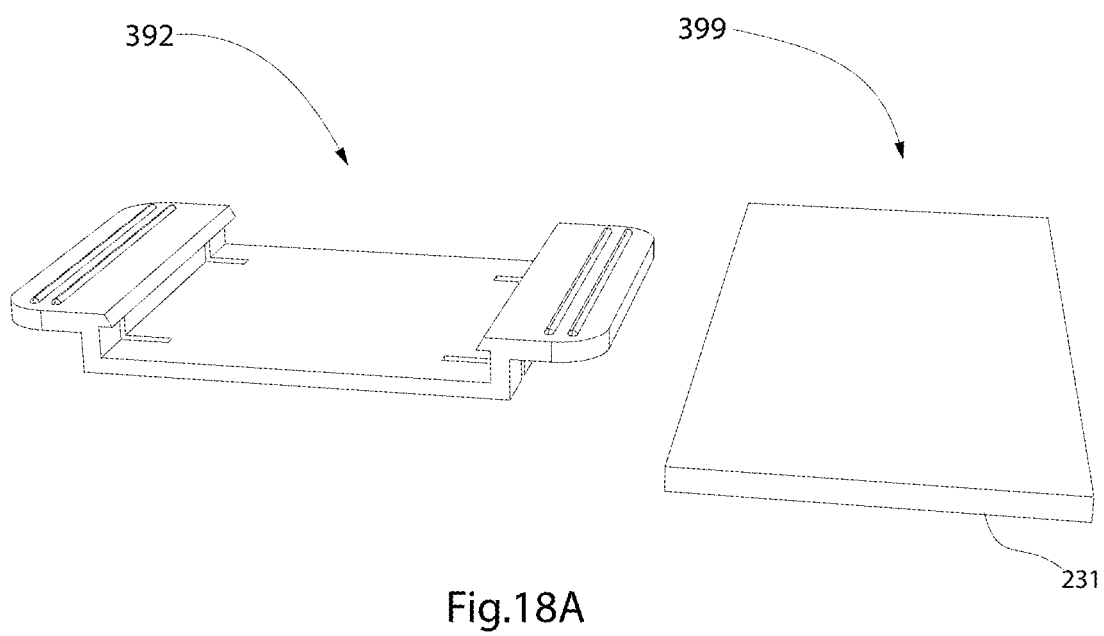
FIGS. 18A-18E are perspective views illustrating a process of attaching headphones to a leg locking assembly in accordance with an embodiment of the present disclosure.

FIGS. 18A-18E demonstrate the principle used in the deformable leg locking assembly depicted in FIG. 17. As shown in FIG. 18A, the male latch member is initially in a locked, engaged state. The female catch member 399 can be defined by the leg 231 of the headphones. In the illustrated embodiment, the female catch member does not further include any specialized mating or alignment features. However, such features can be added for purposes of improving alignment and or locking of the headphone leg within the male latch member.

Figure 18D:
Figure 18C:
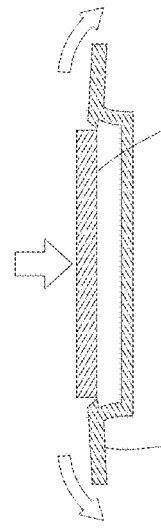
Figure 18B:
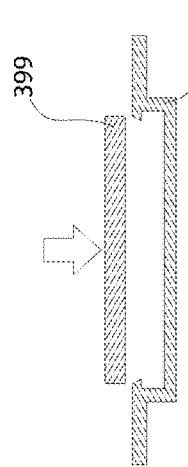
Figure 18E:
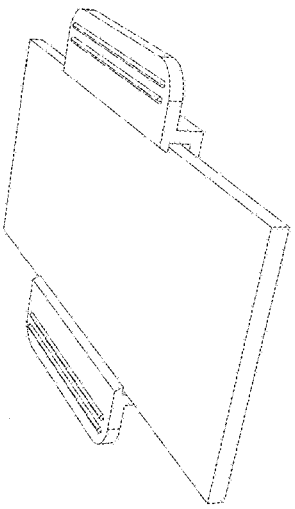

FIGS. 18B-18D are cross-sectional views showing the process of locking the female member 399 within the male member 392. FIG. 18B depicts the female catch member 399 (e.g. leg 231) being urged towards the male member 392. From this position, the female catch member 399 can be lowered into the male latch member 392 as shown in FIG. 18C. As the female catch member 399 is lowered into the male latch member 392, the arms 393 deform outwardly to accommodate the female catch member 399. FIG. 18D shows the male latch member 392 in the engaged, locked position, where the arms 393 have deformed back into their rest position. In the engaged, locked position the arms 393 of the male member 392 surround the female catch member 399 such that the female member 399 is fully received within the cavity 394 of the male member 392. FIG. 18E provides a perspective view of the members 392, 399 in the engaged, locked position The female member 399 can be released from the male member 392 by a user depressing and outer portion of one or more of the arms 393 of the male member 392, thereby deforming the one or more arms 393 into an open, disengaged position. The process of removing the female member 399 can proceed in an opposite manner as the method of installation previously described, i.e. from FIG. 18D to FIG. 18C, and so forth.

The present disclosure is not limited to the specific arrangement of the locking assemblies described herein. For example, the location of the male and female members (e.g. latch and catch) can be reversed such that a latch can be located on the located on the headphones and a catch can be located on the helmet. Additionally, it is contemplated that the headphones and helmet can each include both male and female members.

Figure 19:
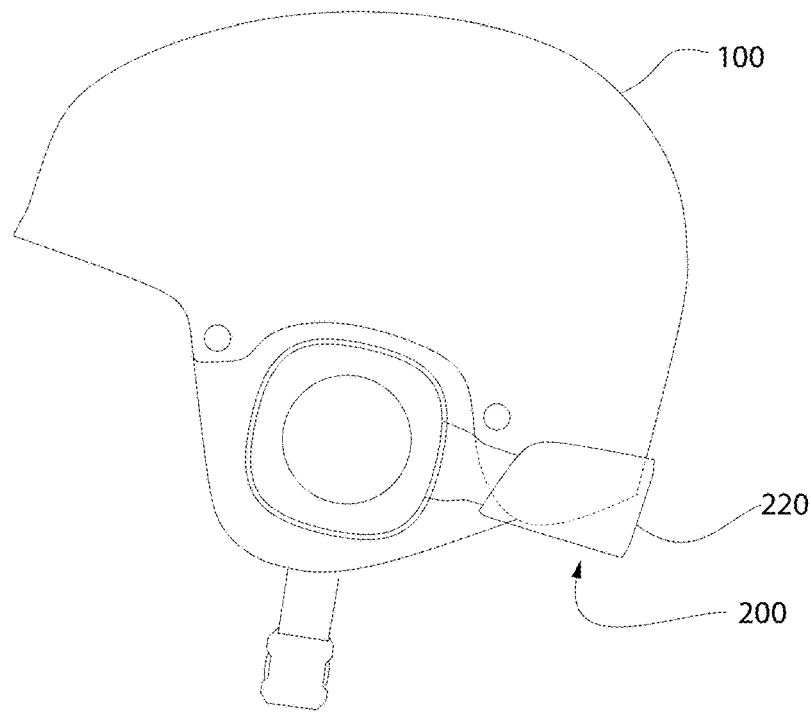
FIG. 19 is a side view of a headphone and helmet assembly in accordance with an embodiment of the present disclosure.

It will be appreciated that the above-described locking mechanisms can be applied to various styles of helmets. Moreover, the helmet can be configured to receive the headphones in various ways. For example, as shown in FIG. 19 the headphones 200 can be located fully outside of the helmet 100. In this embodiment, the helmet 100 may have a soft shell portion that is non-rigid (e.g. pliable). The soft shell portion can correspond to a lower, ear portion of the helmet 100 that is located below an upper, hard shell. This design can advantageously allow for the helmet 100 to act as a barrier between a user's head and the headphones. The soft shell portion may be more comfortable to a user than a helmet 100 having a full hard shell. Furthermore, it is possible to configure the headphones 200 to be removable while a user is wearing the helmet 100. Although this design may increase comfort and ease of attachability of the headphones, protection to a user may be decreased as compared to other helmet 100 and headphone configurations due to, in part, the non-rigid, lower portion of the helmet 100. Another possible disadvantage of this configuration is that the headphones 200 are exposed to possible damage during use as they protrude outside of the helmet 100, and are therefore not protected by the helmet 100.

Figure 20:
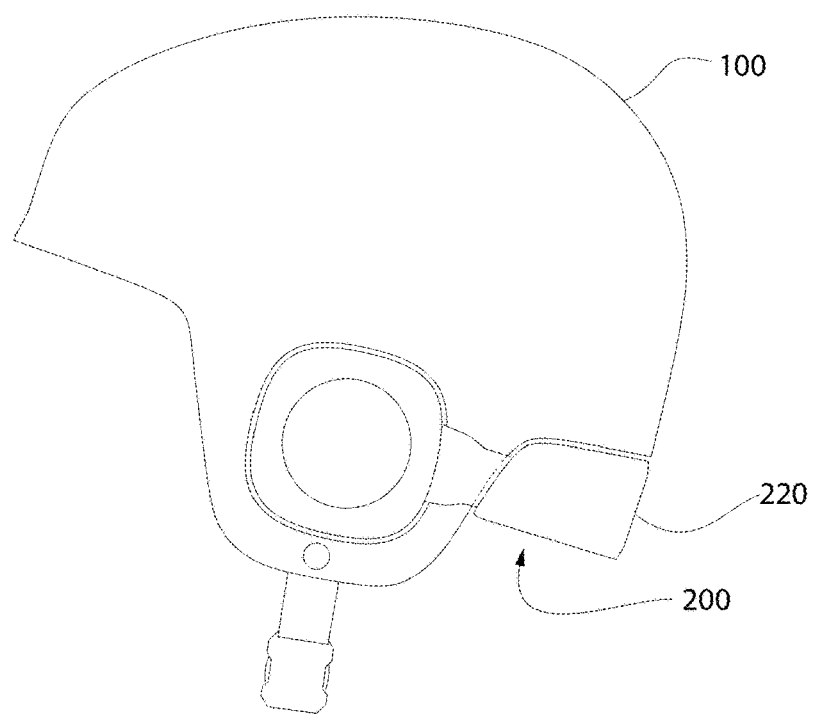
FIG. 20 is a side view of a headphone and helmet assembly where the headphones are located outside of the helmet in accordance with another embodiment of the present disclosure.

Another helmet 100 configuration is shown in FIG. 20, where the headphones 200 are located fully outside of the helmet 100 with a hard shell that fully covers the lower ear portion of the helmet 100. As compared to the prior configuration, the larger hard shell increases protection to the user, and the helmet 100 serves as a barrier between the head and headphones. Similar to the prior configuration, it is possible to configure the headphones 200 to be removable while a user is wearing the helmet 100. However, the headphones 200 are exposed to possible damage during use as they protrude outside of the helmet 100, and are therefore not protected by the helmet 100.

Figure 21:
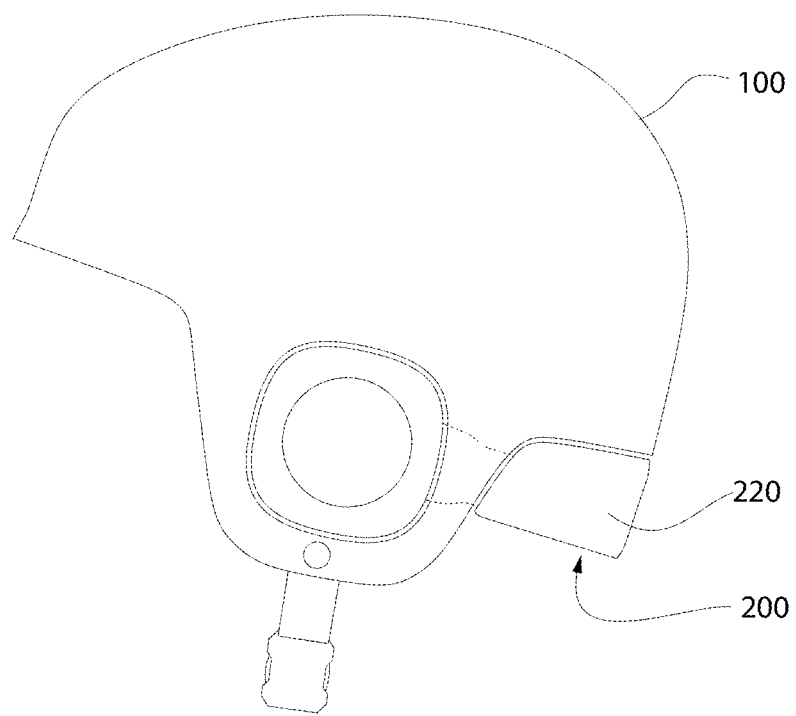
FIG. 21 is a side view of a headphone and helmet assembly where the headphones are located partly outside of the helmet in accordance with another embodiment of the present disclosure.

A further helmet 100 configuration is shown in FIG. 21, where the headphones 200 are located partly inside the shell of the helmet 100, and partly outside the shell of the helmet 100. This design can be employed with a full hard shell, or part hard and part soft shell as previously described. As compared to other helmet 100 and headphone configurations, this design can provide for improved overall protection of the user's head. Moreover, the headphones 200 can be protected from most impacts as only the headband 220 is exposed outside of the helmet 100 shell.

Figure 22:
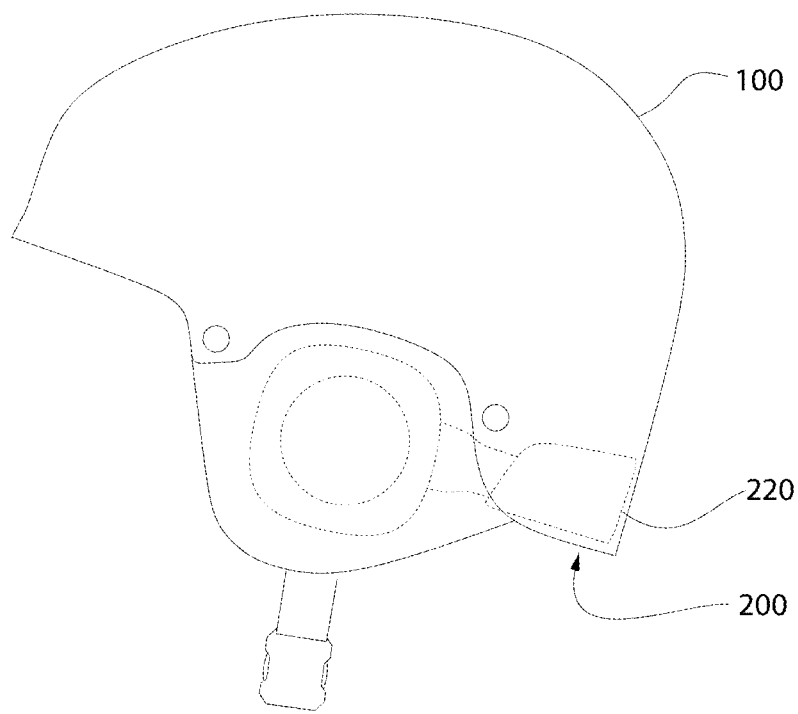
FIG. 22 is a side view of a headphone and helmet assembly where the headphones are located within the helmet in accordance with another embodiment of the present disclosure.

Another helmet 100 configuration is shown in FIG. 22, where the headphones 200 are located fully within the shell of the helmet 100. This design allows for full protection of the headphones 200 within the shell, but can be complex to manufacture due to the need for the helmet 100 to house the headphones 200 in their entirety. Moreover, as the headphones 200, and particularly the headband 220, take up space within the helmet 100, this design can potentially trade protection of the headphones 200 for optimal user protection.

Figure 23A:
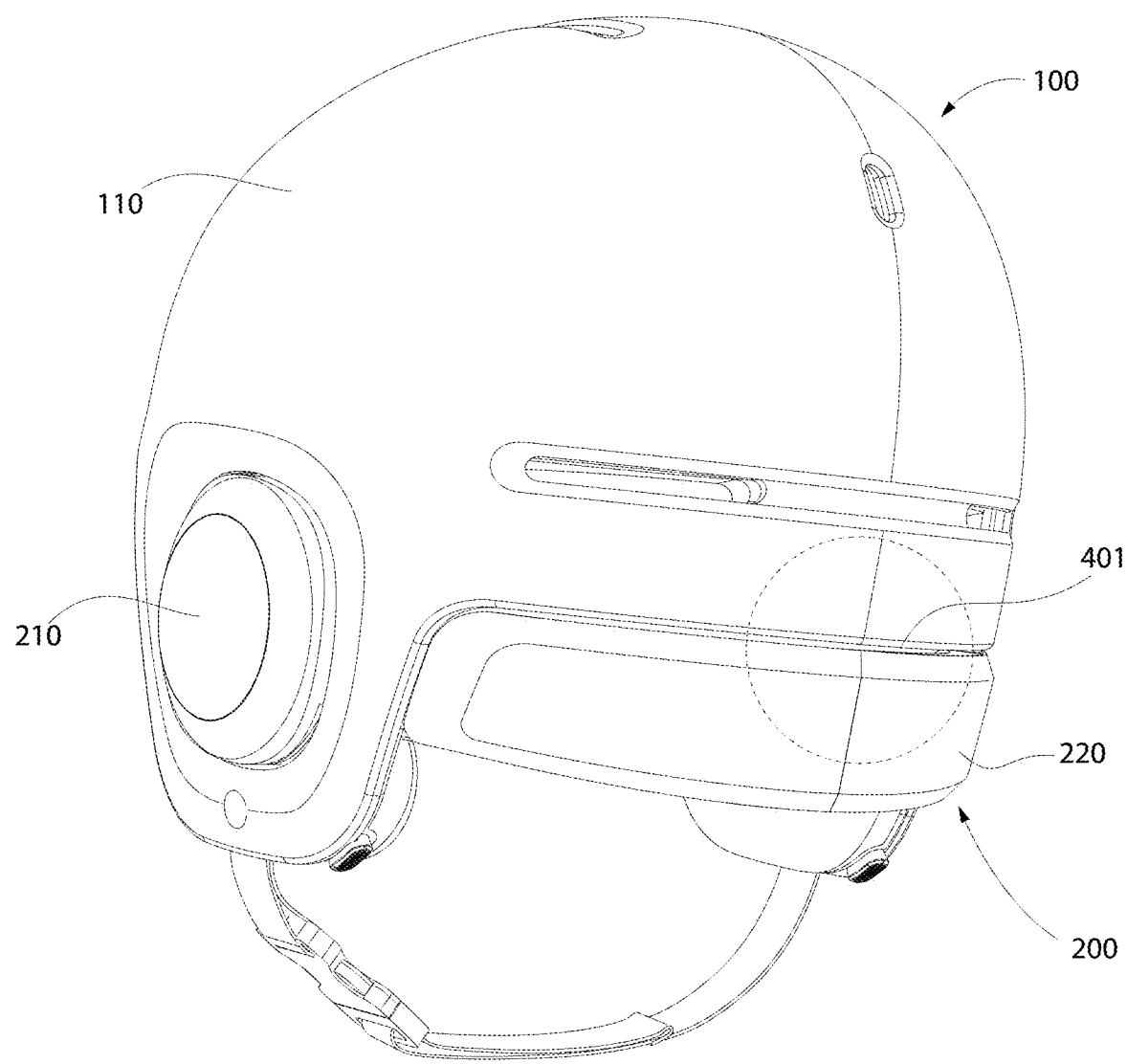
FIG. 23A is a perspective view of a headphone and helmet assembly having an alignment feature in accordance with another embodiment of the present disclosure.
Figure 23B:
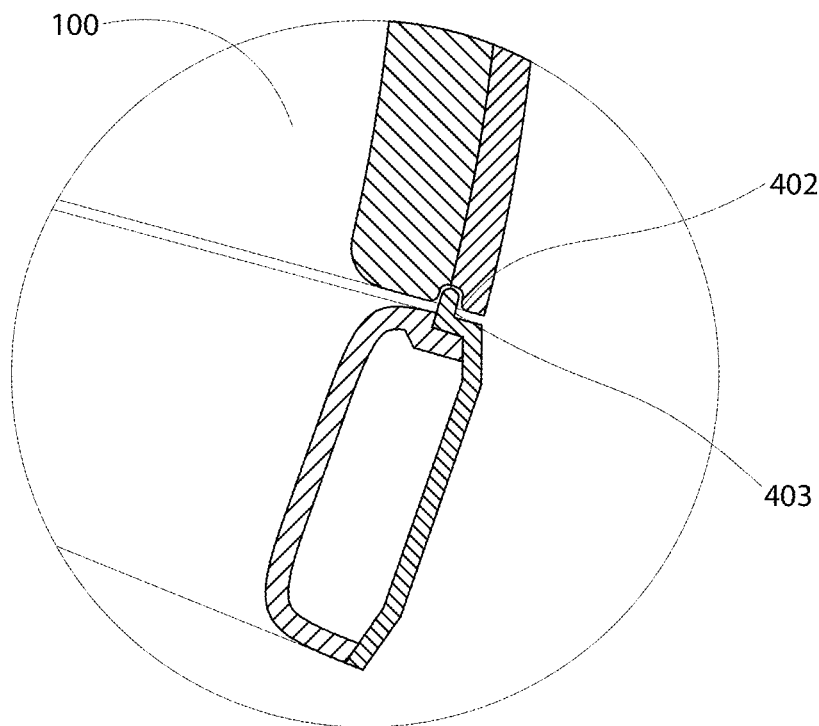
FIG. 23B is a detail cross-sectional view of the alignment feature of FIG. 23A.
Figure 23C:
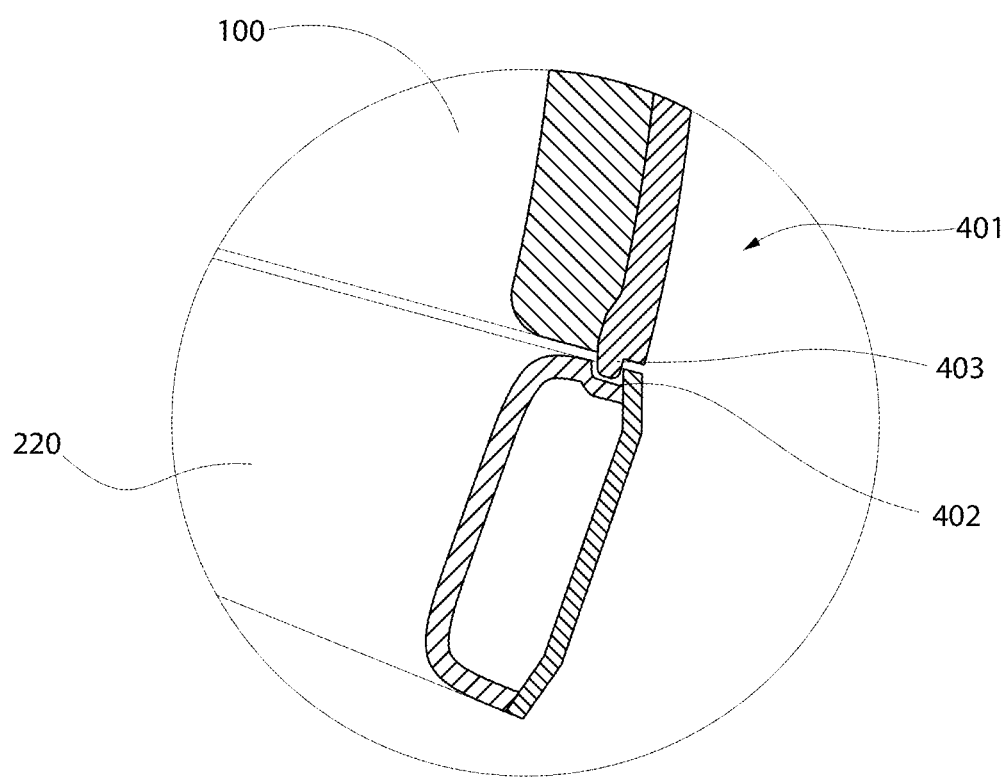
FIG. 23C is a detail cross-sectional view of an alternative embodiment of the alignment feature shown in FIG. 23B.

FIGS. 23A-23C show an example of a headband 220 having an alignment feature that may be used to assist in aligning the headphones 200 relative to the helmet 100. Such an alignment feature can be used in combination with the interlocking assemblies described herein. As shown in FIG. 23A, the headphones may have one or more alignment edges 401, which mate with a corresponding edge of the helmet 100. In one particular embodiment, two side edges and one longitudinal edge of the headphones 200 may mate with corresponding edges of the outer shell 110 of the helmet 100. The outer surface of the headphones may be coplanar or substantially coplanar with the outer surface of the helmet 100 to produce a substantially seamless appearance. In another embodiment, the outer surface of the headphones may be located below the outer surface of the helmet 100 for protection of the headband 220 during impact.

The headband 220 may also include alignment features that interlock to assist in mating the edges of the headband 220 and helmet 100. FIGS. 23B and 23C provide detail views of the headphones including such interlocking alignment features. In FIG. 23B, the helmet 100 includes a female mating member 402 (e.g. recess) and the headphones 200 include a male mating member 403 (e.g. protrusion). In FIG. 23C, the female mating member 402 is located on the headphones 200 and the male mating member 403 is located on the helmet 100. In either embodiment, the male mating member 403 and the female mating member 402 may be located on a side edge of the helmet 100 and headband 220, respectively. For example, the helmet 100 of FIG. 23B includes a recess disposed between an inner layer and outer shell of the helmet 100. However, the recess can be entirely disposed within an inner layer of the outer shell of the helmet 100. As another example, the helmet 100 of FIG. 23C includes a protrusion, which can be made from the outer shell of the helmet 100. However, the protrusion can be made from the inner layer or combinations of the inner and outer layer of the helmet 100. The male mating member and the female mating member interlock with one another in a frictional manner (e.g. "snap-fit").

Figure 24A:
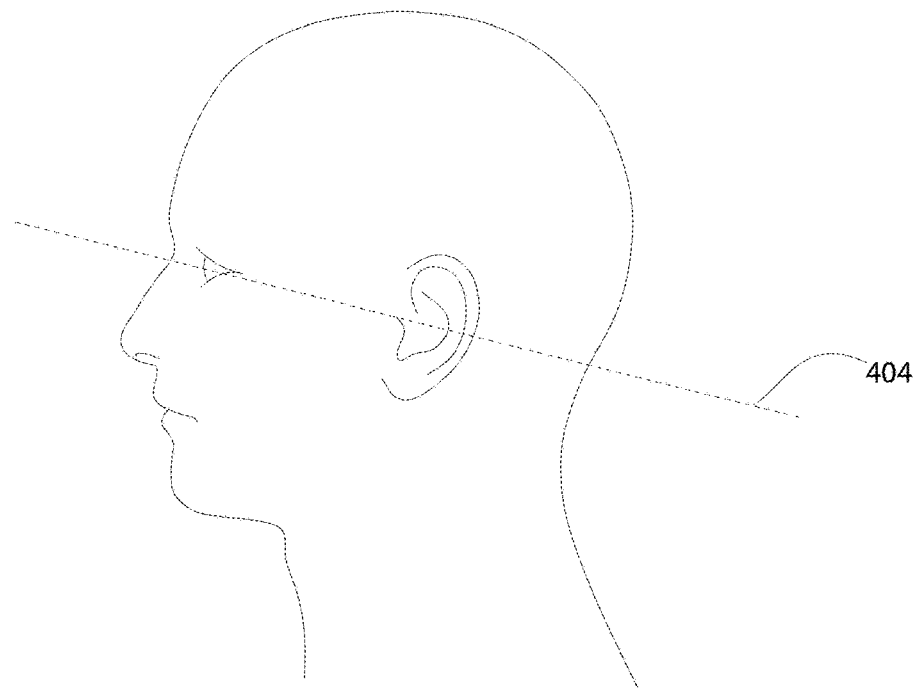
FIGS. 24A-24D are side views illustrating the position that headphones may be positioned on a helmet worn by a user in the locked position in accordance with embodiments of the present disclosure.
Figure 24B:
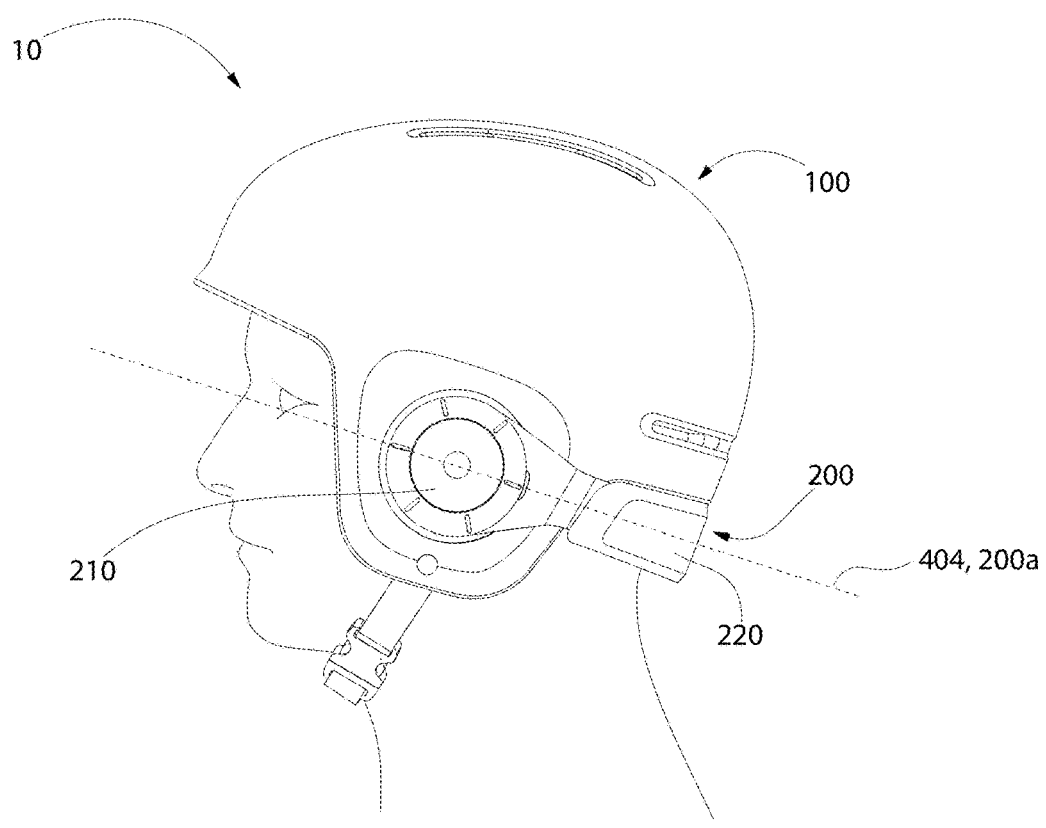

FIGS. 24A-24D illustrate the position that headphones 200 may be held when interlocked with a helmet 100 according to embodiments of the present disclosure. With reference to FIG. 24A and 24B, the headphones 200 can be positioned in a horizontal or substantially horizontal position on the helmet 100 in a locked position. The horizontal position may be aligned with a user's eye and ear. In one example, the headphones 200 can be held in a position (e.g. in a locked position via a locking assembly described herein) where a longitudinal axis 200a of the headphones 200 is approximately aligned with a second axis 404 that follows the user's eye and ear. The longitudinal axis 200a of the headphones 200 can be an axis that goes along the center of each ear cup 210 to a central apex of the headband 220.

Figure 24C:
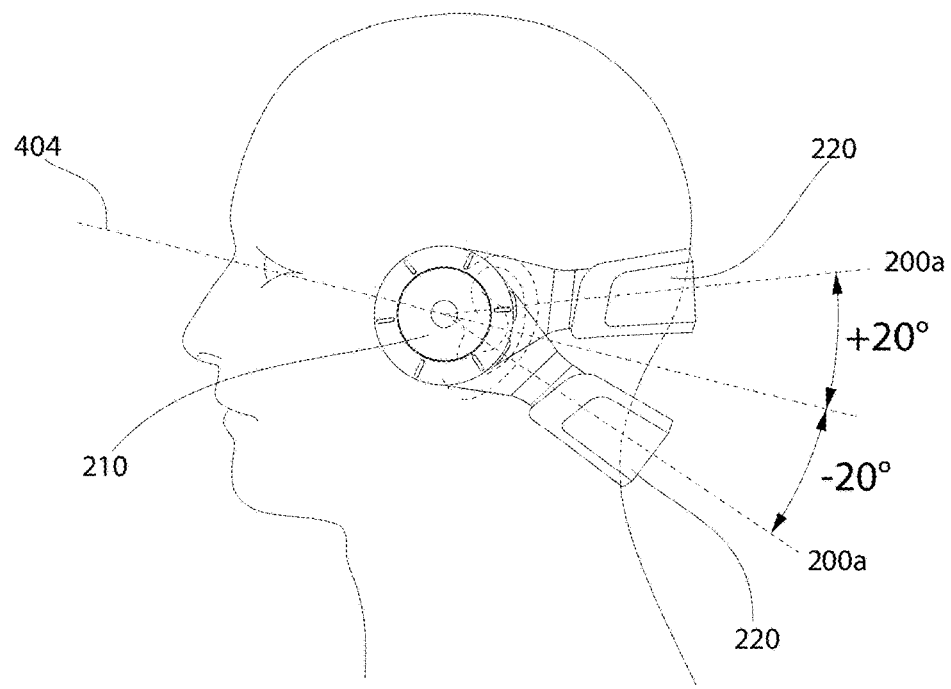

According to FIG. 24C, the headphones 200 can be held (e.g. in a locked position via a locking assembly described herein) such that its longitudinal axis 200a lies at an angle that is ±20° from the second axis 404 of the user. In other embodiments, the headphones 200 can be held such that its longitudinal axis 200a lies at an angle that is ±15°, ±10°, or ±5° from the second axis of the user.

Figure 24D:
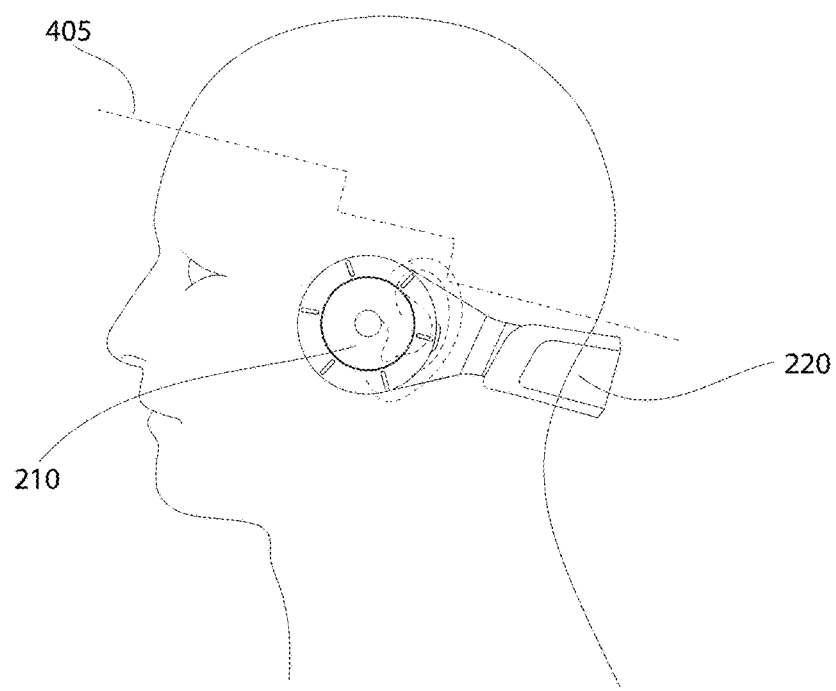

Recreational sports helmets are subject by the established certifications (e.g. ASTM 2040, EN 1077A) to protect the head above a defined impact line 405 as shown in FIG. 24D. In order to satisfy such certifications, headphones should not interfere with the impact area of the helmet 100 (e.g. by being located within the impact line 405, which for example could take up space used for energy absorption and protection). According to embodiments of the present disclosure, the headphones 200 are held such that the headphones 200 may be locked in a position that is outside of the defined impact line 405.

The present disclosure may also allow for the headphones to be positioned such that the user can control music directly from the headphones. In such embodiments, the headphones may be externally accessible, for example, by being disposed through one or more portions of the helmet (e.g.

through an ear cup aperture as previously described) while the headphones are in a locked position on the helmet.

Figure 25A:
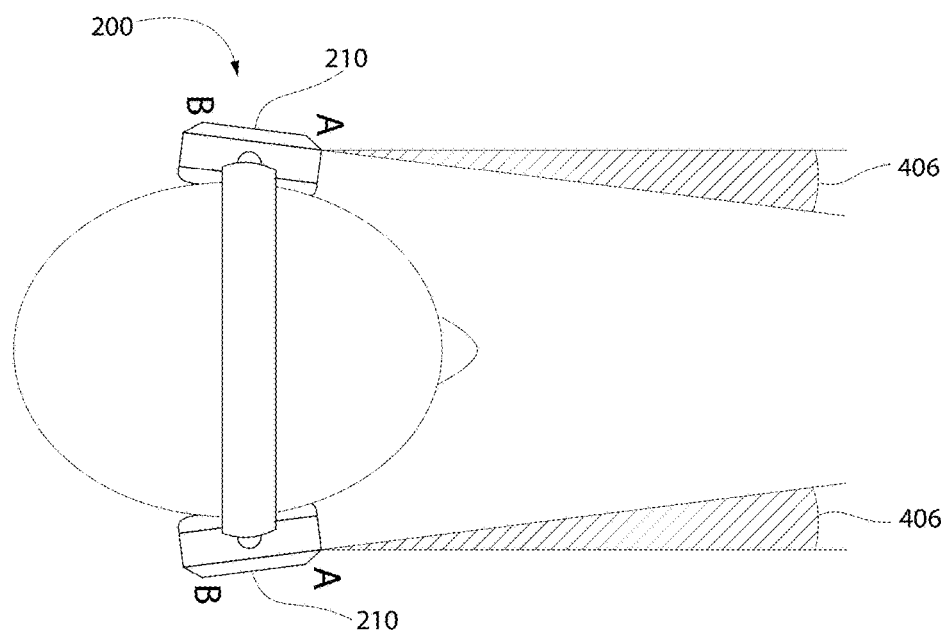
FIG. 25A is a top view illustrating the position that headphones are worn on a user without a helmet in accordance with an embodiment of the present disclosure.

One issue with integrating headphones and a helmet as described herein may be caused due to differences in the surface angle of a user's head and the surface angle of a helmet. The headphones described in the present disclosure may be worn directly by a user (i.e. without a helmet), or be worn by the user in combination with a helmet (e.g. as held in a locked position via by a locking assembly). FIG. 25A shows the angle 406 of the ear cups 210 (defined by the axis along points A and B) relative to a user when the user is wearing the headphones without a helmet. When headphones are worn over the top of a user's head, the shape of the head requires the ear cups 210 to be rotated (e.g. toward the front of the user's head) to accommodate the angle of the head in a comfortable manner. This rotation can be provided, for example, by each ear cup 210 being disposed at an angle (e.g. each ear cup 210 being nonparallel to one another) and/or with ear pad foam that will allow the abutting edge of the ear cups 210 to be angled.

Figure 25B:
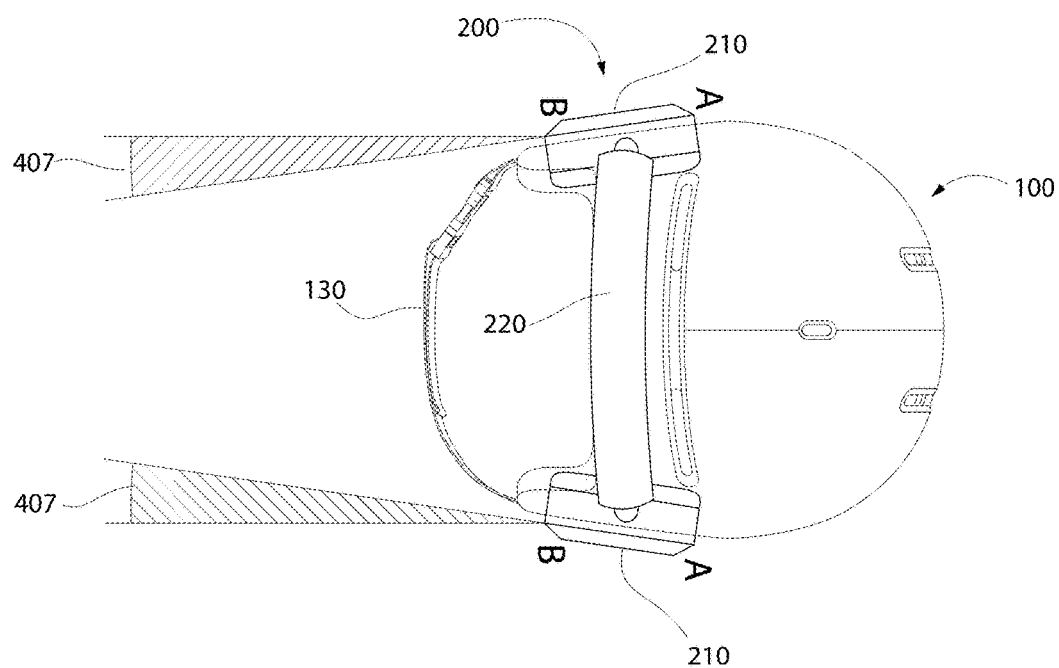
FIG. 25B is a rear view illustrating the position that headphones may be positioned on a helmet worn by a user in the locked position in accordance with an embodiment of the present disclosure.

FIG. 25B shows the angle 407 of the ear cups 210 (defined by the axis along points A and B) relative to a user when the user is wearing the headphones 200 locked with a helmet 100 according to the present disclosure. As opposed to the generally vertical position of FIG. 25A, the present disclosure may allow for the headphones 200 to be locked onto a helmet 100 in a substantially horizontal position. However, when the headphones are held in the horizontal position, the outer surface of the helmet 100 is angled 407 in an opposite manner than the angle 406 that headphones are held directly on a user's head (i.e. without a helmet). If the headphone ear cups 210 are not rotated in this "opposite" manner (e.g. in a position that is generally parallel to the outer surface of the helmet 100, then the headphones 200 would either protrude outside or inside of the helmet 100 thereby compromising safety, comfort, and/or aesthetics. Thus, the ear cups 210 of the present disclosure can allow for rotation of the ear cups 210 in both directions shown in FIGS. 25A and 25B. In one embodiment, differences in rotation can be accommodated by providing ear cups 210 that rotate relative to the legs, for example, with a swivel connection as shown in FIG. 3B. According to another embodiment, shown in FIGS. 25C-25E, the headphones 200 may be mounted such that each ear cup 210 is in a fixed, non-parallel position, and can allow for tilting of an inner portion of each ear cup 210.

Figure 25C:
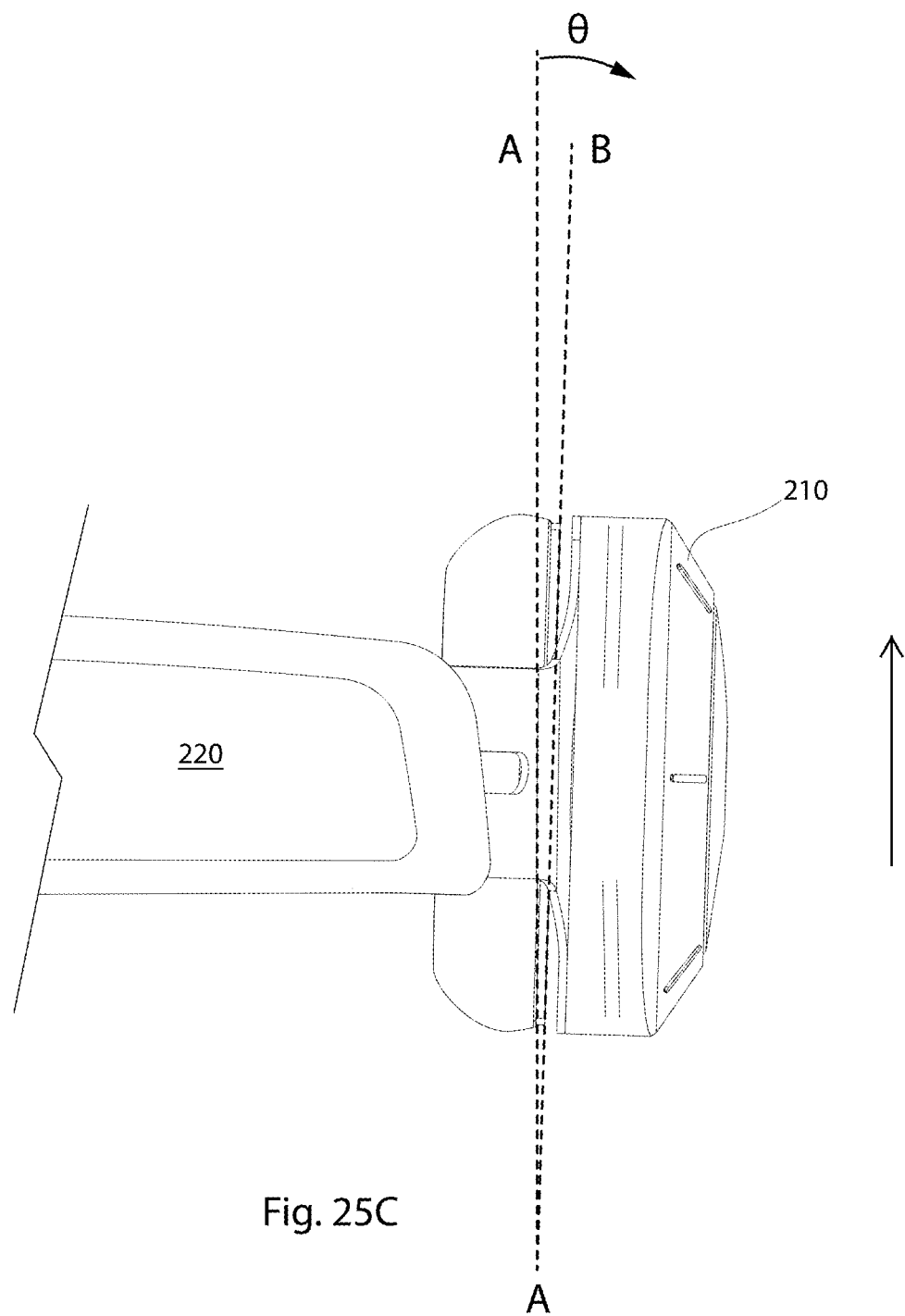
FIG. 25C is a top view illustrating an ear cup having a fixed, angled orientation in accordance with an embodiment of the present disclosure.

FIG. 25C is a top view of a single ear cup 210, showing an example where each ear cup 210 is fixed at an angle θ between axis A-A and axis A-B, where the arrow is pointing toward the front of the headphones 200 when worn by a user (i.e. the arrow is directed toward the user's face). Axis A-A can correspond to the vertical axis between each ear cup 210 (i.e. perpendicular), and axis A-B can correspond to the axis of the helmet shell 110. The angled fixed position of the ear cup 210, i.e. at angle θ can be achieved by each leg 231 having a lower angled piece, adjacent the headphones 200. For example, each leg 231 may begin at a parallel position relative to one another, adjacent the headband 220, and then begin to tilt at a location adjacent each ear cup 210. The fixed angle θ can be compared to a perfectly "neutral" position relative to the headband. According to some embodiments, angle θ may be a single, fixed angle between 2-5°. In one particular embodiment, the angle θ may be 3°.

Figure 25D:
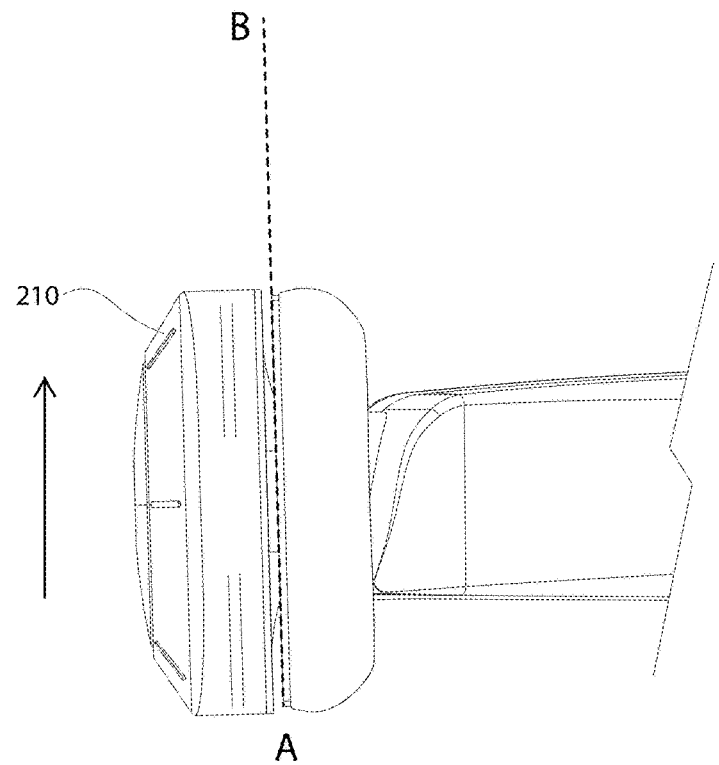
FIGS. 25D-25E are bottom views illustrating a pivotable ear cup in accordance with an embodiment of the present disclosure.
Figure 25E:
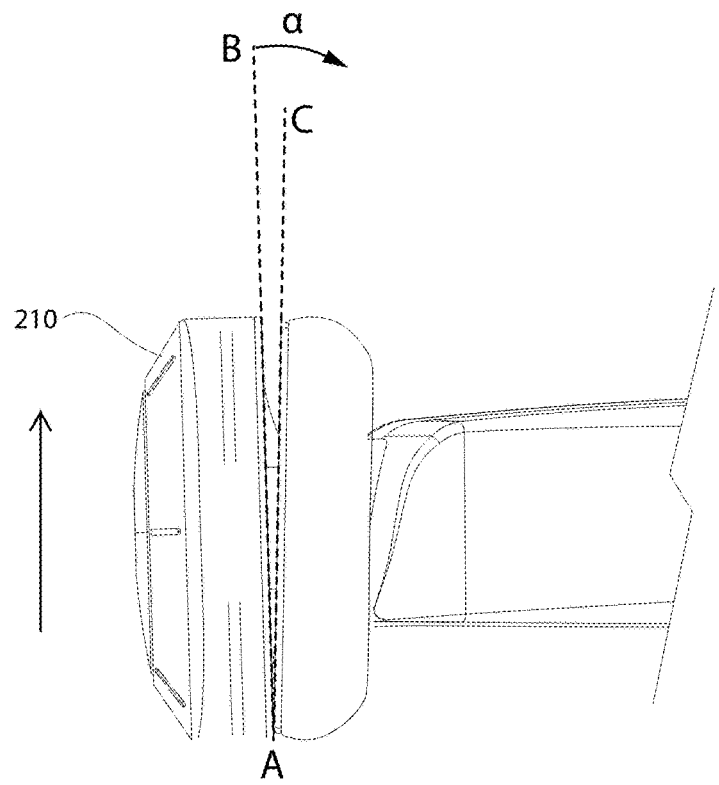

FIGS. 25D and 25E are bottom views of a single ear cup 210, showing an example where each ear cup 210 is freely tiltable an angle a between axis A-B and axis A-C, where the arrow pointing toward the front of the headphones when worn by a user (i.e. the arrow is directed toward the user's face). Axis A-B can correspond to the fixed axis shown in FIG. 25C (e.g. which may correspond to the axis of the helmet shell), and axis A-C shows the inner piece of the ear cup 210 angled into a tilted position for use on a user's head (i.e. without a helmet). The titled position of the ear cup 210 shown in FIG. 25E can be achieved, for example, by having the inner piece of the ear cup 210 mounted at a swivel relative to the outer piece of the ear cup 210. An example of a swivel mount 417 is shown in FIG. 26B. According to some embodiments, the inner piece of the ear cup 210 may be configured to pivot up to a maximum angle a between 2-6°. In one particular embodiment, the angle α may be 4°.

According to another embodiment of the present disclosure, headphones can include an input control device for controlling a media source (e.g. an electronic device such as an electronic media player. In one embodiment, the input control device may be one or more rotatable ear cups. One or more sensors may be used to monitor the position and/or a change of position of an ear cup. The one or more sensors can send a signal to control the electronic device.

Figure 26A:
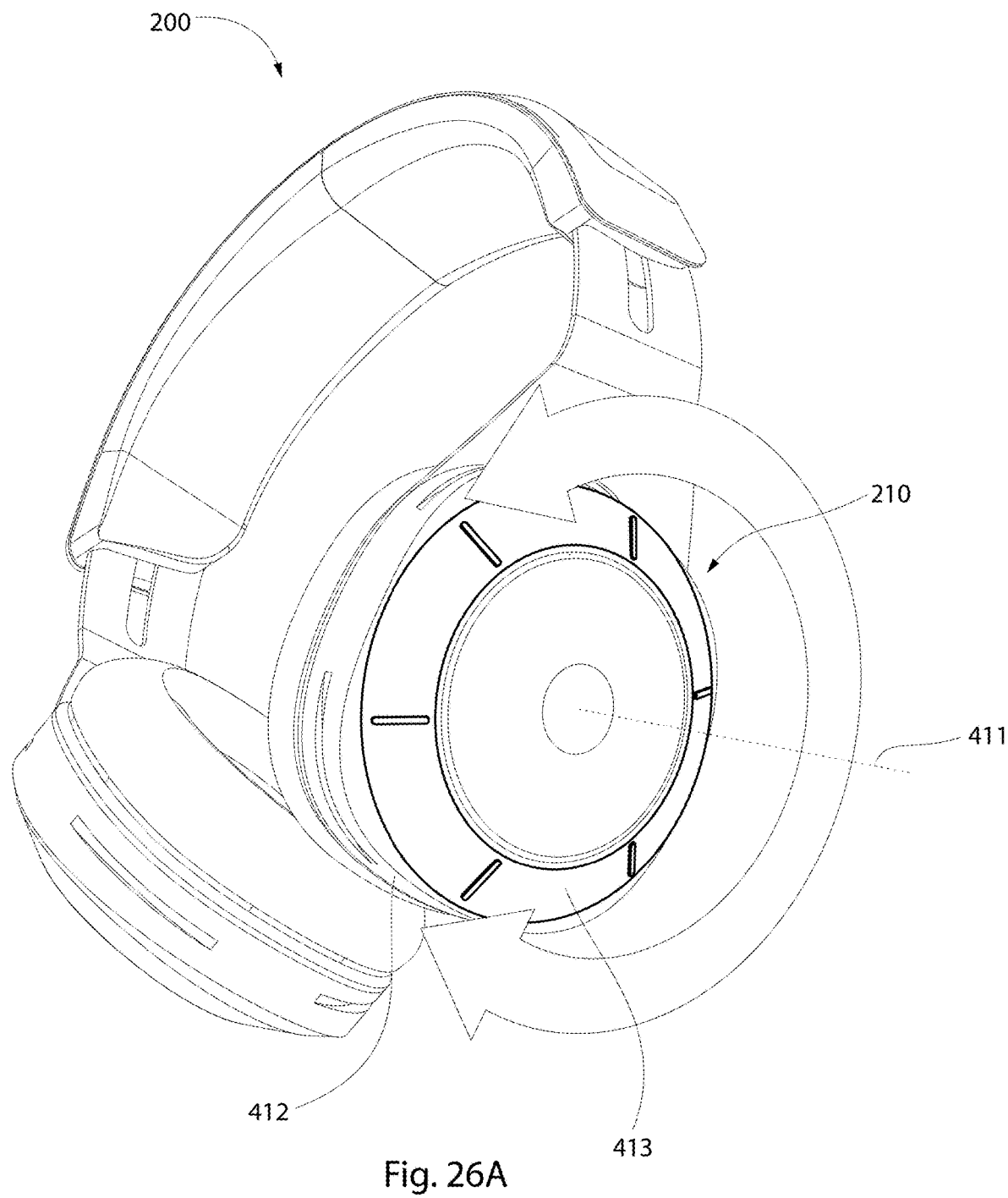
FIG. 26A is a perspective view of headphones having a rotatable ear cup that serves as an input control device in accordance with an embodiment of the present disclosure.
Figure 26B:
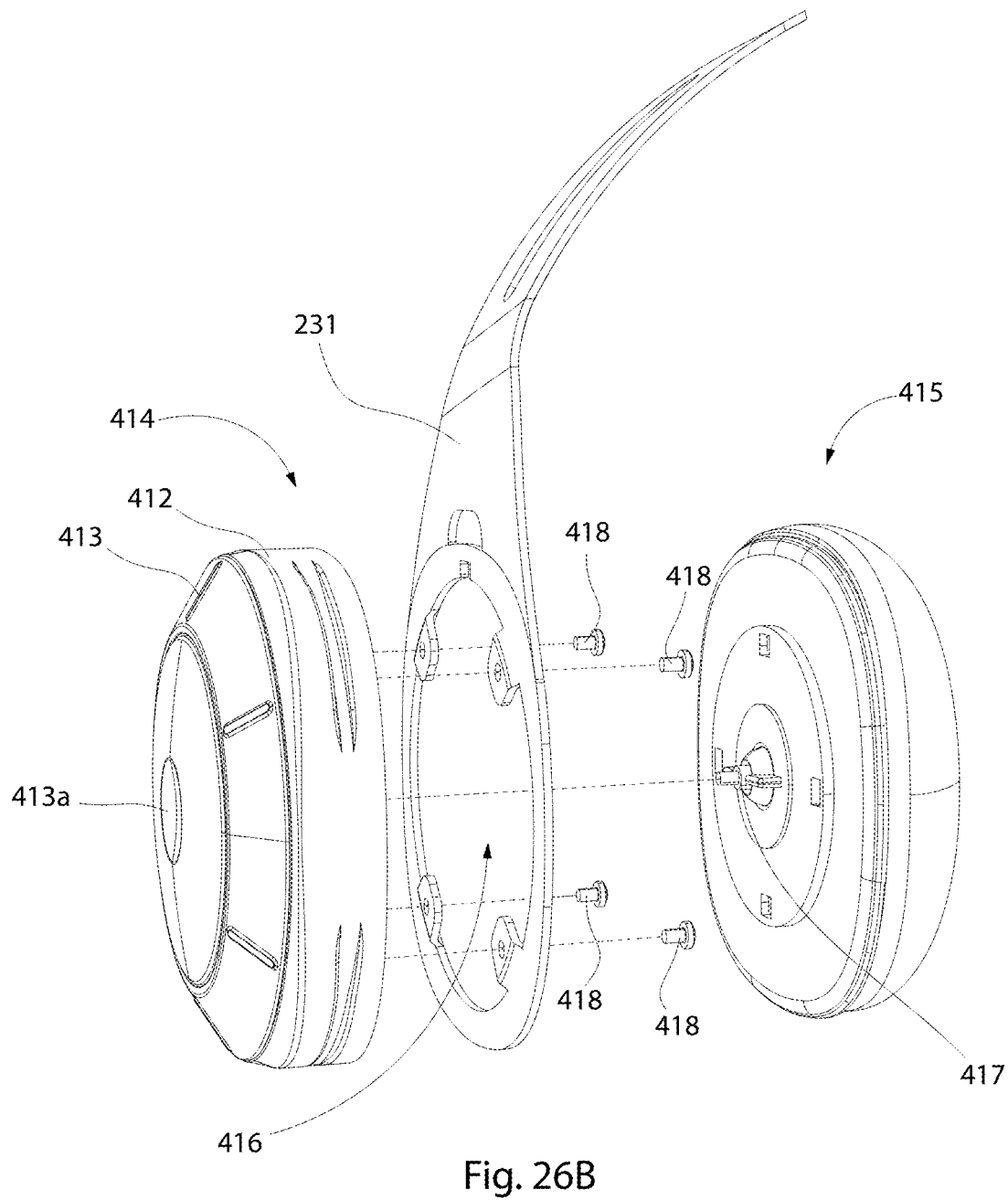
FIG. 26B is an exploded view of the headphones of FIG. 26A.

FIG. 26A shows an embodiment of headphones having a rotatable ear cup 210 that serves as an input control device for controlling an electronic device (i.e. media input for the headphones). The rotatable ear cup 210 may include a housing 412 and a rotational element 413, which rotates about axis 411.

FIG. 26B is an exploded view of an assembly of the headphones 200 shown in FIG. 26A. The ear cup 210 may be defined by an outer piece 414 and an inner piece 415. The outer piece 414 can be fixed to the leg 231 (e.g. via fasteners 418), and the inner piece 415 may be pivotally mounted to the outer piece 414 via swivel 417, which extends through central aperture 416. The inner piece 415 can be used to house one or more speakers (not shown) of the headphones 200.

Figure 27A:
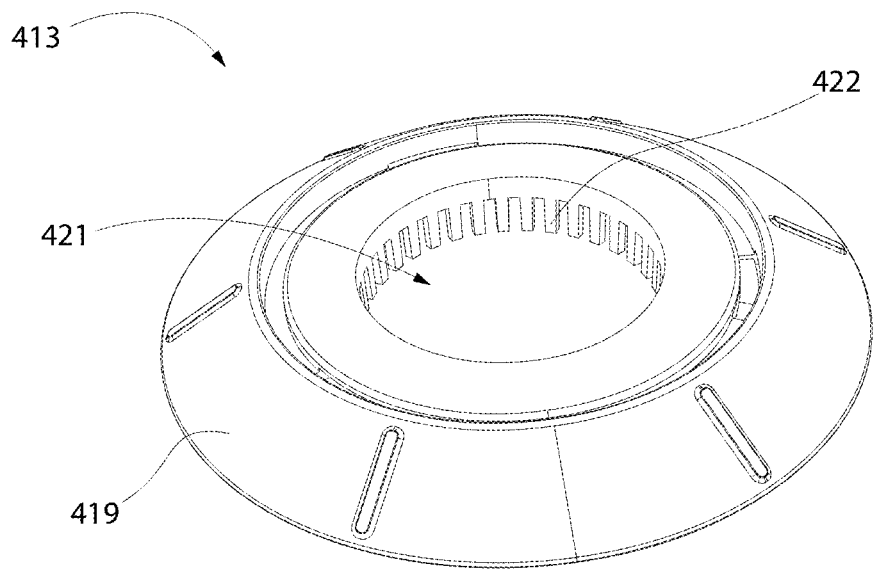
FIGS. 27A-27B are perspective views of a rotational element of the rotatable ear cup shown in FIG. 26A.
Figure 27B:
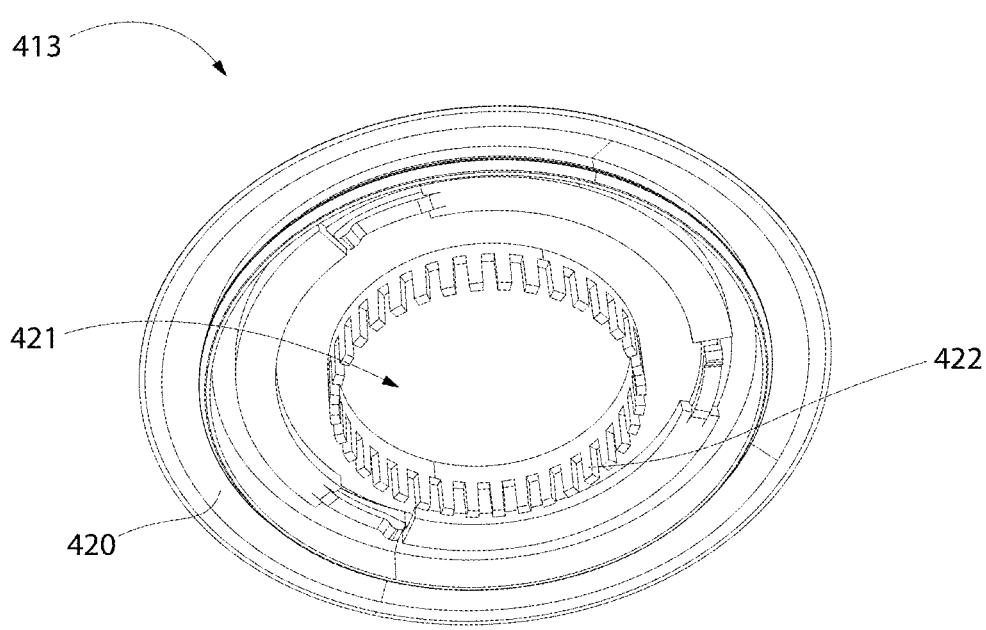

FIG. 27A and 27B are perspective views of an exemplary rotational element 413 of an ear cup 210. The rotational element 413 includes an outer surface 419, an inner surface 420, and aperture 421, and a plurality of teeth 422. The plurality of teeth 422 may be disposed at regular intervals about the aperture 421. In one particular example, there may be 30 teeth 422 on the rotational element 413. In another embodiment, there may be more than 30 teeth on the rotational element 413.

Figure 28A:
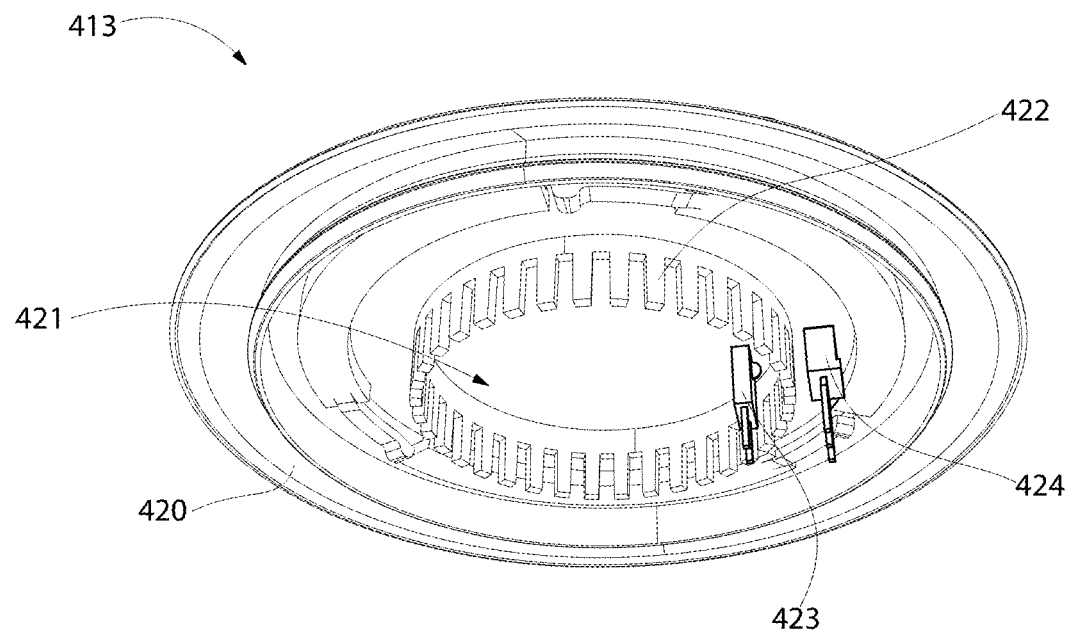
FIG. 28A is a perspective view of a rotational element and sensor elements of the rotatable ear cup shown in FIG. 26A.
Figure 28B:
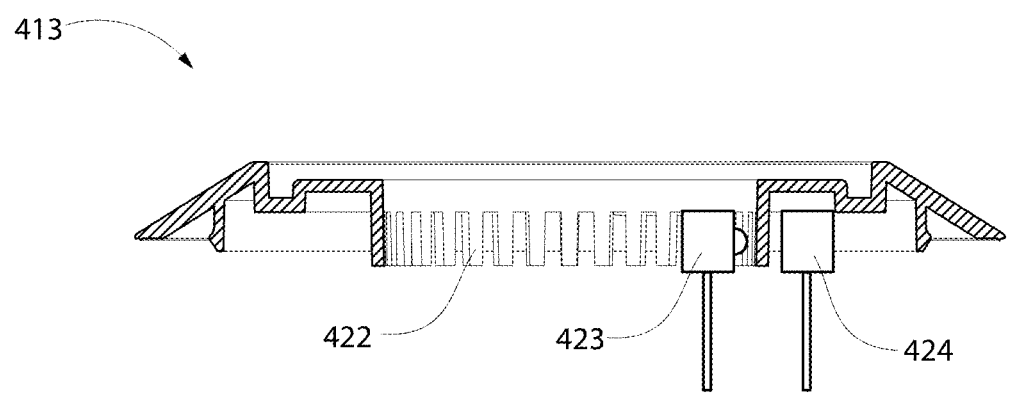
FIG. 28B is a cross-sectional view of a rotational element and sensor elements of the rotatable ear cup shown in FIG. 28A.

FIGS. 28A and 28B show a sensor arrangement configured to detect a change of position of the rotational element 413 relative to housing 412. The sensor arrangement may include a first sensor element 423 and a second sensor element 424 disposed on the housing 412. In one particular embodiment, the sensor arrangement may be a photosensor pair. For example, the first sensor 423 may be a light source (e.g. an infrared emitter) and the second sensor 424 may be one or more, or two or more, light detectors (e.g. two phototransistors). As illustrated in the cross-sectional view of 28B, the first sensor 423 and second sensor 424 may be positioned on opposite sides of the plurality of teeth 422. It should be realized that the sensor elements can be reversed in position.

Figure 29:
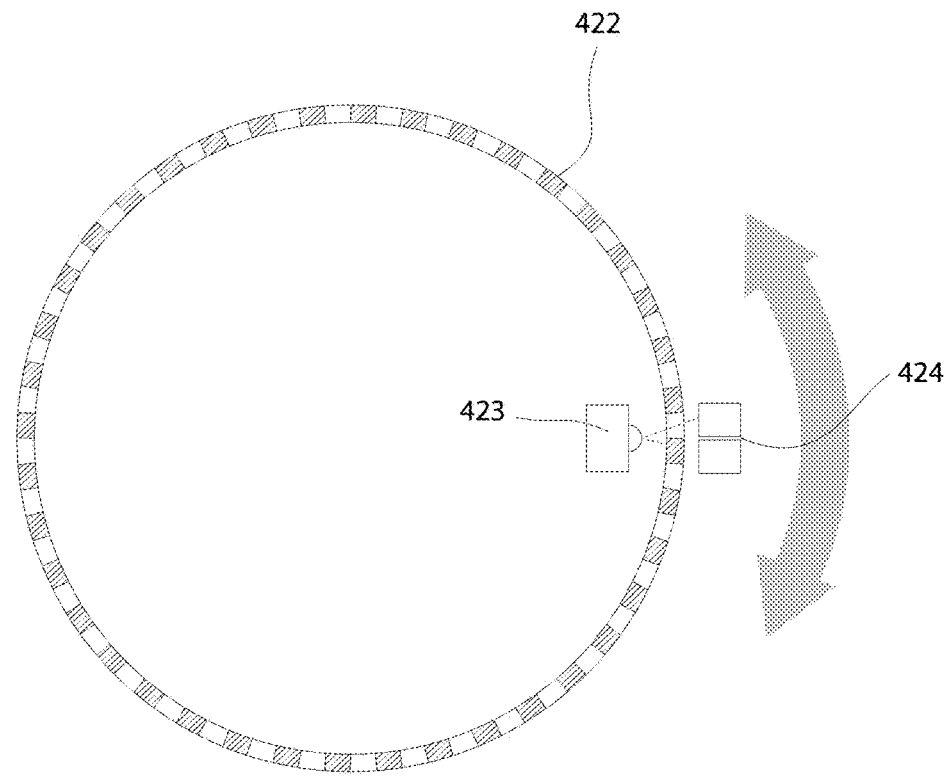
FIG. 29 is a top schematic view of a rotational element and sensor elements of the rotatable ear cup shown in FIG. 27C.

FIG. 29 is a schematic representation showing that as the rotational element 413 turns, light emission L (e.g. infrared emission) is blocked intermittently by the plurality of teeth 422. The relative position of the sensor elements 423, 424 can cause changes in a signal received by the sensor arrangement in order to determine a change in position as well as direction, speed, and/or acceleration.

Figure 30:
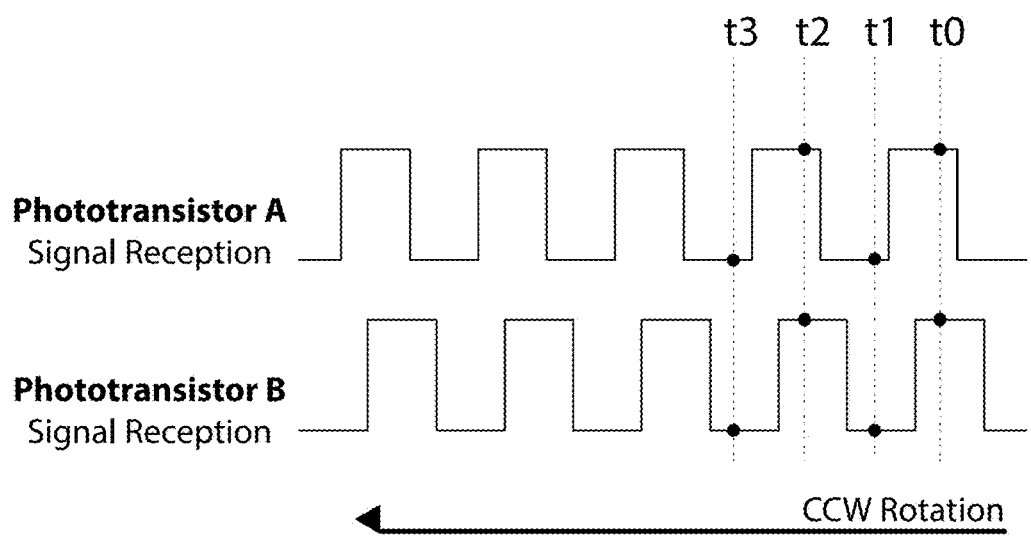
FIG. 30 is a graph of signal receptions of sensor elements in accordance with an embodiment of the present disclosure.

FIG. 30 illustrates signal receptions of respective first and second sensor elements (e.g. of exemplary phototransistors A and B) over time during rotation of the rotational element relative to the base. As can be seen, differences in received signals between phototransistors A and B at a current time (e.g. t0, t1, t2, t3) can be used to determine the direction of travel of the rotational element. Thus, the sensor arrangement can be used to detect a change of position as well as detect a direction of rotation. The sensor arrangement can have various applications for controlling electronic device. One particular example is to control the volume of media being played through the speakers of the headphones.

Figure 31:
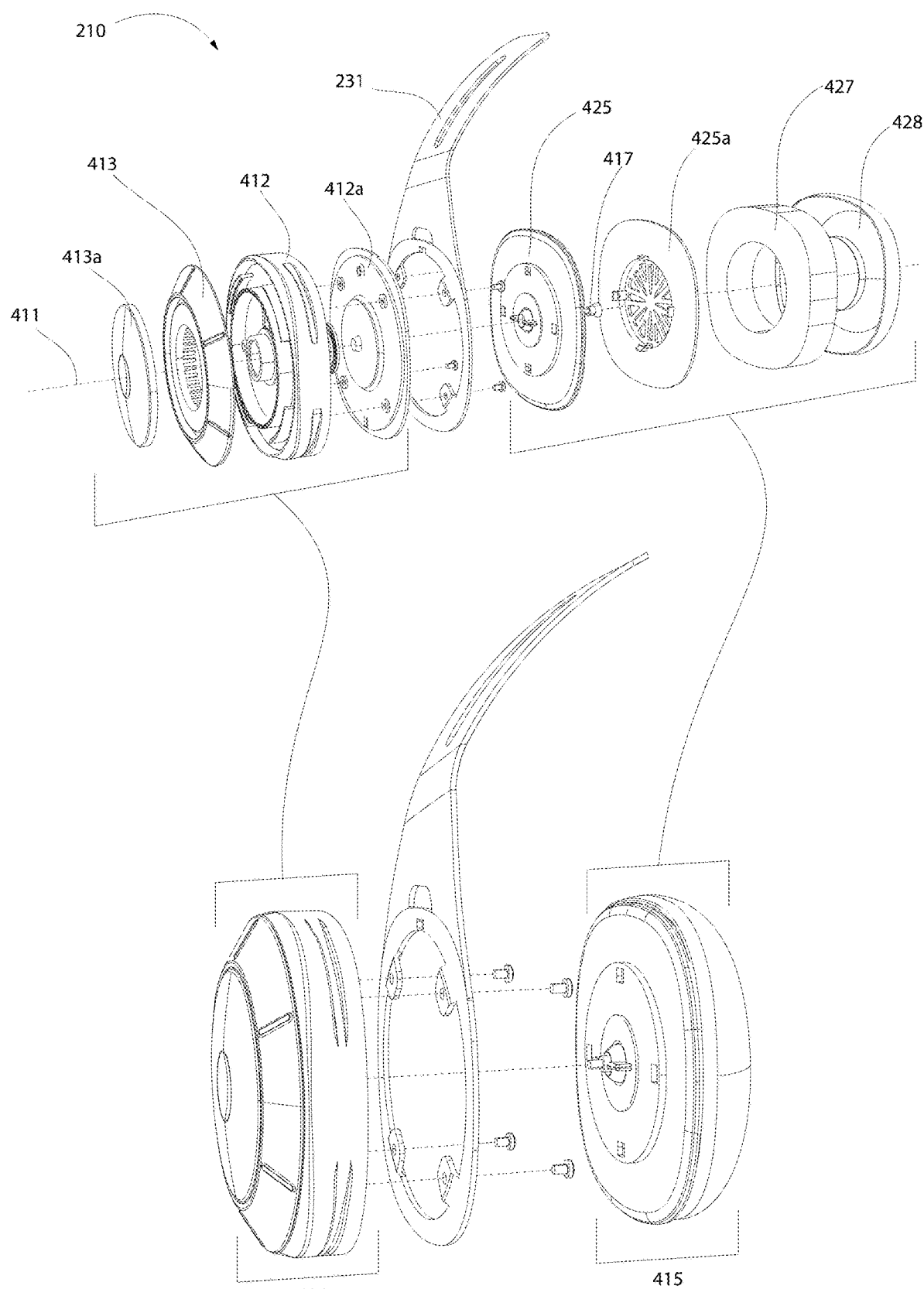
FIG. 31 is an exploded view of headphones having a rotatable ear cup that serves as an input control device in accordance with an embodiment of the present disclosure.

FIG. 31 is an exploded view of a specific embodiment of a side of headphones having a rotatable ear cup 210 that serves as an input control device in accordance with an embodiment of the present disclosure. The headphones may include an ear cup 210 having an outer piece and an inner piece.

The outer piece can include a rotational element and a selection button that serve as an input control device. A sensor (not shown) may be used to detect rotation (e.g. movement, direction, speed, and/or acceleration), which may be used to serve as an input control device for controlling a media source rotates about axis 411. The selection button can be a depressible element that moves along axis 411, into the rotational element. A sensor can be positioned to sense when the selection button is depressed, and the selection button may be biased toward an undepressed state. A housing 412 can receive the rotational element, and include a housing cap 412a. The housing cap and/or housing may be attached to a leg 231.

The inner piece can include a frame 425 that houses a swivel 417 (e.g. a tilt screw) for connecting the inner piece to the outer piece. The frame 425 may have a cover 425a that can house a driver or speaker (not shown) therein. Ear cup padding 427 (e.g a compressible material, such as foam) may be attached to the frame 425. An outer ear cup layer 428 can house the ear cup padding relative to the frame 425.

While the disclosure has been described in connection with exemplary embodiments, the detailed description is not intended to limit the scope of the disclosure to the particular forms set forth. The disclosure is intended to cover such alternatives, modifications and equivalents of the described embodiment as may be included within the scope of the claims.

What is claimed is:

1. A detachable assembly, comprising:
    headphones, including a headband, ear cups, and a housing, the housing defining legs extending between each of the ear cups and the headband;
    a helmet for protecting a user, the helmet including a chinstrap, a shell, and a pair of ear cup receiving apertures extending fully through the shell; and
    a locking assembly configured to removably attach the headphones to the helmet in a locked position;
    wherein the pair of ear cup receiving apertures is configured to receive a respective one of the ear cups at least partially therethrough in the locked position;
    wherein in the locked position, the headphones are locked horizontally such that a longitudinal axis of the headphones lies at a locking angle that is ±20° from a second axis, the second axis extending from the user's eye and ear when the helmet is on the user, the longitudinal axis extending between each ear cup to a central apex of the headband.

2. The detachable assembly of claim 1, wherein at least a portion of the legs of the headphones is disposed within the shell of the helmet in the locked position.

3. The detachable assembly of claim 1, wherein the locking assembly includes one or more male members and one or more female members configured to mate with the one or more male members;
    wherein the one or more male members are located adjacent the pair of ear cup receiving apertures; and
    wherein the one or more female members are located on the ear cups.

4. The detachable assembly of claim 1, wherein the helmet includes a trough disposed on an inner surface of the helmet, the trough receiving one or more of the following in the locked position: the legs and the headband of the helmet.

5. The detachable assembly of claim 1, wherein the locking assembly includes one or more flexible mating features that interlock with one another in a frictional manner.

6. The detachable assembly of claim 1, wherein the locking assembly is a biased locking assembly having one or more slidable male members that are biased toward one or more female members in the locked position.

7. The detachable assembly of claim 1, wherein the locking assembly is a rotational locking assembly having one or more rotational latch members and one or more fixed catch members.

8. The detachable assembly of claim 7, wherein the one or more rotational latch members includes two disks, each of the two disks having a central aperture defined by an inner edge, each of the two disks being rotationally mounted about each of the pair of ear cup receiving apertures between an unlocked position and the locked position;
    wherein the central aperture is concentric with each of the pair of ear cup receiving apertures.

9. The detachable assembly of claim 8, wherein in the unlocked position, the inner edge is located fully about each one of the pair of ear cup receiving apertures, and in the locked position, the inner edge is positioned at least partially within each one of the pair of ear cup receiving apertures.

10. The detachable assembly of claim 9, wherein the one or more rotational latch members includes an arm disposed outside of the helmet and configured to allow the user to rotate the one or more rotational latch members between the locked position and the unlocked position.

11. The detachable assembly of claim 10, wherein in the locked position the arm is located closer to the headband than in the unlocked position.

12. The detachable assembly of claim 7, wherein rotating the ear cups about the pair of ear cup receiving apertures moves the headphones between an unlocked position and the locked position.

13. The detachable assembly of claim 1, wherein the locking assembly is a sliding locking assembly having one or more male latch members defined by a pair of parallel, linear protrusions fixed adjacent to each one of the pair of ear cup receiving apertures, and one or more female catch members that receive the one or more male latch members in the locked position.

14. The detachable assembly of claim 1, further comprising a headphone leg locking assembly including male latch members located on the helmet, and female catch members located on the legs, the male latch members being configured to removably attach the legs to an inner surface of the helmet in the locked position.

15. The detachable assembly of claim 1, wherein at least one of the ear cups includes an inner piece and an outer piece, the inner piece housing a speaker for playing sound from the media source, the outer piece including a rotational element configured to rotate relative to the inner piece;

wherein rotation of the rotational element controls operation of a media source.

16. The detachable assembly of claim 15, further comprising:
a first sensor element and a second sensor element;
wherein the rotational element includes a plurality of teeth, the first sensor element and a second sensor element disposed on opposite sides of the plurality of teeth.

17. The detachable assembly of claim 16, wherein the first sensor element includes an infrared emitter and the second sensor element includes two or more light detectors.

18. The detachable assembly of claim 1, wherein a bottom portion of the legs adjacent each of the ear cups are angled such that the ear cups are fixed in a non-parallel position that corresponds to an angled outer surface of the shell of the helmet;
wherein each of the ear cups are angled relative to the headband at an angle between 2-5°.

19. A helmet assembly, comprising:
headphones, including a headband, ear cups, and a housing, the housing defining legs extending between each of the ear cups and the headband;
a helmet for protecting a user, the helmet including a chinstrap, a shell, and a pair of ear cup receiving apertures extending fully through the shell; and
a locking assembly configured to removably attach the headphones to the helmet in a locked position;
wherein the pair of ear cup receiving apertures is configured to receive a respective one of the ear cups at least partially therethrough in the locked position; and
wherein at least one of the ear cups includes an input control device configured to control a media source;
wherein at least one of the ear cups includes an inner piece and an outer piece, the inner piece housing a speaker for playing sound from the media source, the outer piece including a rotational element configured to rotate relative to the inner piece;
wherein rotation of the rotational element controls operation of a media source.

* * * * *